US010275710B1

(12) United States Patent
Teredesai et al.

(10) Patent No.: US 10,275,710 B1
(45) Date of Patent: Apr. 30, 2019

(54) MACHINE LEARNING MODEL REPOSITORY

(71) Applicant: KenSci Inc., Seattle, WA (US)

(72) Inventors: Ankur Teredesai, Bellevue, WA (US); James Andrew Marquardt, Tacoma, WA (US); Chris James Rizzuto, Renton, WA (US); Tyler John Hughes, Seattle, WA (US)

(73) Assignee: KenSci Inc., Seattle, WA (US)

( * ) Notice: Subject to any disclaimer, the term of this patent is extended or adjusted under 35 U.S.C. 154(b) by 5 days.

(21) Appl. No.: 15/799,322

(22) Filed: Oct. 31, 2017

(51) Int. Cl.
| | |
|---|---|
| *G06N 3/08* | (2006.01) |
| *G06K 9/62* | (2006.01) |
| *G16H 15/00* | (2018.01) |
| *G06N 20/00* | (2019.01) |

(52) U.S. Cl.
CPC .............. *G06N 3/08* (2013.01); *G06K 9/6218* (2013.01); *G06K 9/6232* (2013.01); *G16H 15/00* (2018.01); *G06K 2009/6238* (2013.01); *G06N 20/00* (2019.01)

(58) Field of Classification Search
CPC ................................................. G06F 17/30321
See application file for complete search history.

(56) References Cited

U.S. PATENT DOCUMENTS

| 2009/0144213 | A1* | 6/2009 | Patil ..................... G06K 9/6253 706/46 |
| 2016/0155069 | A1* | 6/2016 | Hoover ................... G06Q 30/06 706/12 |

OTHER PUBLICATIONS

'An introduction to distributed and parallel computing': Chrichlow, Prentice Hall, 1988.*
'Active GP classifiers for handwritten digit recognition': Teredesai, 2008, researchgate.*
'An introduction to distributed and parallel computing': Crichlow, 1988.*

* cited by examiner

*Primary Examiner* — Robert A Cassity
*Assistant Examiner* — Peter D Coughlan
(74) *Attorney, Agent, or Firm* — John W. Branch; Lowe Graham Jones PLLC

(57) ABSTRACT

Embodiments are directed towards a machine learning repository for managing machine learning (ML) model envelopes, ML models, model objects, or the like. Questions and model objects may be received by a ML model answer engine. Machine learning (ML) model envelopes may be received based on the questions. The model objects may be compared to parameter models associated with the ML model envelopes. ML model envelopes may be selected based on the comparison such that the model objects satisfy the parameter models of each of the selected ML model envelopes. ML models included in each selected ML model envelope may be executed to provide score values for the model objects and the score values may be included in a report.

30 Claims, 14 Drawing Sheets

MACHINE LEARNING MODEL REPOSITORY

TECHNICAL FIELD

The present invention relates generally to machine learning and, more particularly, but not exclusively to methods for sharing or distributing machine learning models.

BACKGROUND

Machine learning is increasingly playing a larger and more important role in developing or improving the understanding of complex systems. As machine learning techniques have matured, machine learning has rapidly moved from the theoretical to the practical. Combined with the advent of big-data technology, machine learning solutions are being applied to a variety of industries and applications that until now were difficult, if not impossible to effectively reason about. As such, there has been an explosion of the development of different types of machine learning models that may be used predicting outcomes for different system. In some cases, organizations may develop many machine learning models that may be directed to different question spaces. Also, organizations may be interested in borrowing machine learning models, sharing machine learning models, cooperatively developing machine learning models, or the like. However, machine learning models may often be developed using custom handcrafted designs tailored for individual data sets or for a specific problems. Accordingly, practical re-use, sharing, or the like, of machine learning models may be difficult and impractical. Thus, it is with respect to these considerations and others that the invention has been made.

BRIEF DESCRIPTION OF THE DRAWINGS

Non-limiting and non-exhaustive embodiments of the present innovations are described with reference to the following drawings. In the drawings, like reference numerals refer to like parts throughout the various figures unless otherwise specified. For a better understanding of the described innovations, reference will be made to the following Detailed Description of Various Embodiments, which is to be read in association with the accompanying drawings, wherein.

DETAILED DESCRIPTION OF VARIOUS EMBODIMENTS

Figure 1:
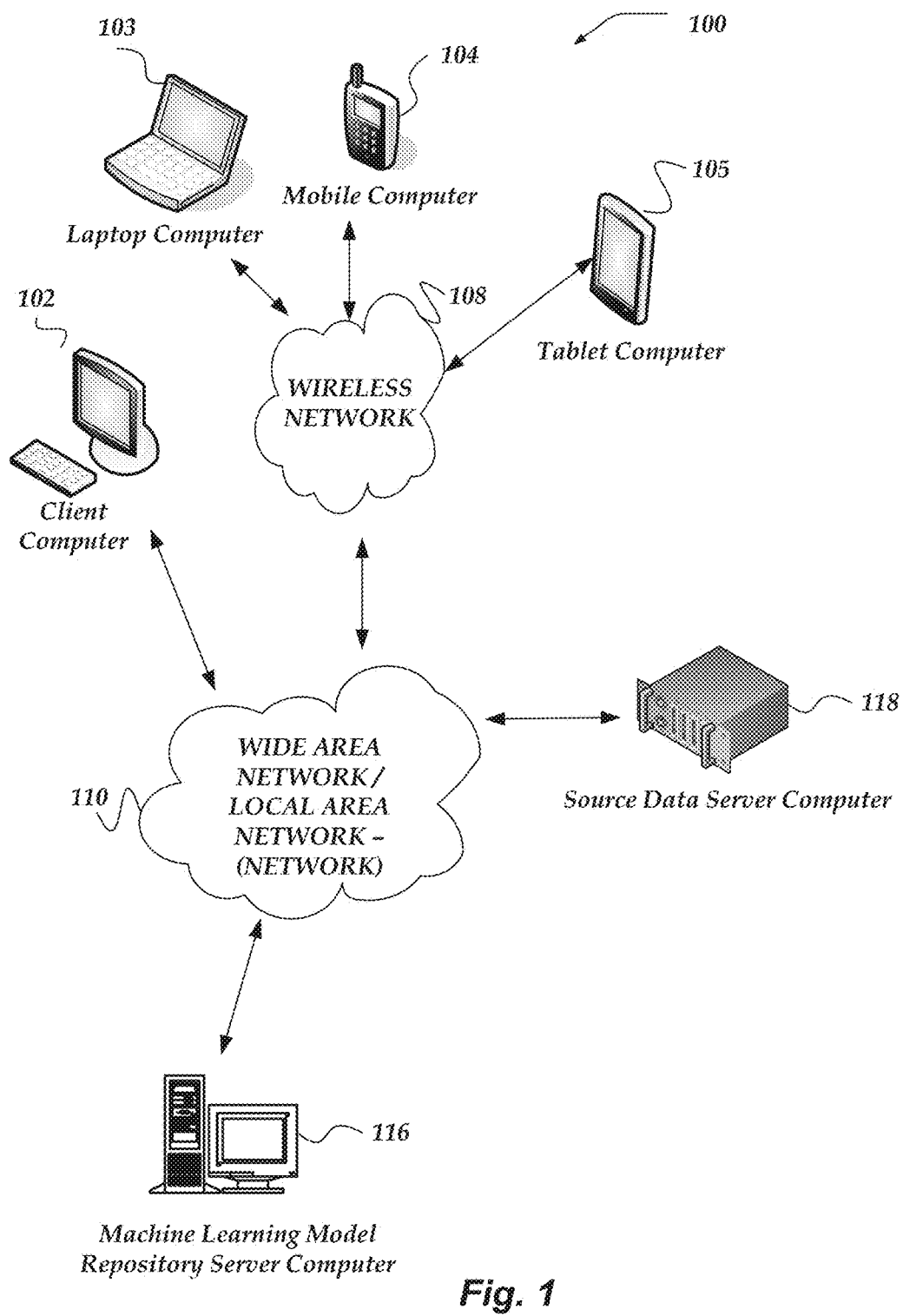
FIG. 1 illustrates a system environment in which various embodiments may be implemented.

Various embodiments now will be described more fully hereinafter with reference to the accompanying drawings, which form a part hereof, and which show, by way of illustration, specific exemplary embodiments by which the invention may be practiced. The embodiments may, however, be embodied in many different forms and should not be construed as limited to the embodiments set forth herein; rather, these embodiments are provided so that this disclosure will be thorough and complete, and will fully convey the scope of the embodiments to those skilled in the art. Among other things, the various embodiments may be methods, systems, media or devices. Accordingly, the various embodiments may take the form of an entirely hardware embodiment, an entirely software embodiment or an embodiment combining software and hardware aspects. The following detailed description is, therefore, not to be taken in a limiting sense.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. Also, throughout the specification and the claims, the use of "when" and "responsive to" do not imply that associated resultant actions are required to occur immediately or within a particular time period. Instead they are used herein to indicate actions that may occur or be performed in response to one or more conditions being met, unless the context clearly dictates otherwise. In addition, throughout the specification, the meaning of "a," "an," and "the" include plural references. The meaning of "in" includes "in" and "on."

For example, embodiments, the following terms are also used herein according to the corresponding meaning, unless the context clearly dictates otherwise.

As used herein the term, "engine" refers to logic embodied in hardware or software instructions, which can be written in a programming language, such as C, C++, Objective-C, COBOL, Java™, PHP, Perl, Python, JavaScript, Ruby, VBScript, Microsoft .NET™ languages such as C#, and/or the like. An engine may be compiled into executable programs or written in interpreted programming languages. Software engines may be callable from other engines or from themselves. Engines described herein refer to one or more logical modules that can be merged with other engines or applications, or can be divided into sub-engines. The engines can be stored in non-transitory computer-readable medium or computer storage device and be stored on and executed by one or more general purpose computers, thus creating a special purpose computer configured to provide the engine.

As used herein, the terms "raw data set," or "raw data" refer to data sets provided by an organization that may represent the items to be included ingested for use in a machine learning repository. In some embodiments raw data may be provided in various formats. In simple cases, raw data may be provided in spreadsheets, databases, csv files, or the like. In other cases, raw data may be provided using structured XML files, tabular formats, JSON files, or the like. In one or more of the various embodiments, raw data in this context may be the product one or more preprocessing operations. For example, one or more pre-processing operations may be executed on information, such as, log files, data dumps, event logs, database dumps, unstructured data, structured data, or the like, or combination thereof. In some cases, the pre-processing may include data cleansing, filtering, or the like. The particular pre-processing operations may be specialized based on the source, context, format, veracity of the information, or the like.

As used herein, the term "raw data objects" refer to objects that comprise raw datasets. For example, if a raw dataset is comprised of a plurality of tabular record sets, the separate tabular record sets may be considered raw data objects.

As used herein, the term "model object" refers to an object that models various characteristics of an entity or data object. Model objects may include one or more model object fields that represent features or characteristics. Model objects, model object fields, or model object relationship may be governed by a model schema.

As used herein, the term "model schema" refers to a schema that defines model object types, model object features, model object relationships, or the like, that may be supported by the machine learning repository. For example, raw data objects are transformed into model objects that conform to a model schema supported by the machine learning repository.

As used herein, the term "data model" refers to a data structure that represents one or more model objects and their relationships. A data model will conform to a model schema supported by the machine learning repository.

As used herein, the term "parameter model" refers to a data structure that represents one or more model objects and the relationships that a ML model envelop or ML model may be arranged to support. A data model that includes model objects may be provided to a ML model if the data model satisfies the requirements of the ML model's parameter model.

As used herein, the terms "machine learning model" or "ML model" refer to a machine learning model that is arranged for scoring or evaluating model objects. The particular type of ML model and the questions it is designed to answer will depend on the application for which the ML model is designed. ML models are associated with parameter models that define model objects that the ML model supports.

As used herein, the terms "machine learning model envelope," or "ML model envelope" refer to a data structure that includes one or more ML models and a parameter model. A ML model envelope may be arranged to include the modules, code, scripts, programs, or the like, for implementing its one or more included ML models.

The following briefly describes the various embodiments to provide a basic understanding of some aspects of the invention. This brief description is not intended as an extensive overview. It is not intended to identify key or critical elements, or to delineate or otherwise narrow the scope. Its purpose is merely to present some concepts in a simplified form as a prelude to the more detailed description that is presented later.

Briefly stated, embodiments are directed towards a machine learning repository for managing machine learning (ML) model envelopes, ML models, model objects, or the like. In one or more of the various embodiments, ML model answer engine may be instantiated to various actions as described below. In one or more of the various embodiments, providing query information based on the question and the model schema. And, in some embodiments, executing the query information to provide the one or more model objects.

In one or more of the various embodiments, one or more questions and one or more model objects may be received by the ML model answer engine such that the one or more model objects may be part of a data model that conforms to a model schema. In one or more of the various embodiments, receiving the one or more model objects may include providing the one or more raw data model objects in real-time. And, in some embodiments, employing the ingestion engine to transform the one or more raw data objects into one or more model objects.

In one or more of the various embodiments, a plurality of machine learning (ML) model envelopes may be received based on the one or more questions.

In one or more of the various embodiments, the data model may be compared to parameter models associated with each of the plurality of ML model envelopes such that the comparison includes a traversal of the data model and one or more of the parameter models. In one or more of the various embodiments, comparing the data model to the parameter models may include, employing one or more indices to identify model objects that match the parameter models of the selected one or more ML model envelopes such that each model object identified using the one or more indices may be omitted from the one or more traversal paths of the data model.

In one or more of the various embodiments, one or more of the plurality of ML model envelopes may be selected based on the comparison such that the one or more traversal paths corresponding to the one or more model objects satisfy the parameter models of each of the selected one or more ML model envelopes.

In one or more of the various embodiments, one or more ML models included in each selected ML model envelope may be executed to provide score values for the one or more model objects and the score values may be included in a report. In one or more of the various embodiments, executing the one or more ML models may include distributing the execution of the one or more ML models to one or more network computers such that two or more ML models that have an affinity to each other may be distributed to the same network computer.

In one or more of the various embodiments, instantiating a model training engine to perform actions, including: receiving a training data set comprised of a plurality of model objects such that the plurality of model objects include one or more of model objects provided in a customer data set, or model objects provided in a validation data set; and training the one or more of the ML models included in the plurality of ML model envelopes using the training data set.

In one or more of the various embodiments, instantiating an ingestion engine to perform actions, including: receiving one or more raw data objects; and executing one or more ingestion rules to transform the one or more raw data objects into the one or more model objects based on the model schema.

In one or more of the various embodiments, instantiating an ingestion engine to perform actions, including: adding one or more model objects to a customer data set; and modifying one or more other data models that include the added model objects based on their relationships with other previously provided model objects.

Illustrated Operating Environment

FIG. 1 shows components of one embodiment of an environment in which embodiments of the invention may be practiced. Not all the components may be required to practice the invention, and variations in the arrangement and type of the components may be made without departing from the spirit or scope of the invention. As shown, system 100 of FIG. 1 includes local area networks (LANs)/wide area networks (WANs)-(network) 110, wireless network 108, client computers 102-105, machine learning model repository server computer 116, one or more source data server computers 118, or the like.

At least one embodiment of client computers 102-105 is described in more detail below in conjunction with FIG. 2. In one embodiment, at least some of client computers 102-105 may operate over one or more wired and/or wireless networks, such as networks 108, and/or 110. Generally, client computers 102-105 may include virtually any computer capable of communicating over a network to send and receive information, perform various online activities, offline actions, or the like. In one embodiment, one or more of client computers 102-105 may be configured to operate within a business or other entity to perform a variety of services for the business or other entity. For example, client computers 102-105 may be configured to operate as a web server, firewall, client application, media player, mobile telephone, game console, desktop computer, or the like. However, client computers 102-105 are not constrained to these services and may also be employed, for example, as for end-user computing in other embodiments. It should be recognized that more or less client computers (as shown in FIG. 1) may be included within a system such as described herein, and embodiments are therefore not constrained by the number or type of client computers employed.

Computers that may operate as client computer 102 may include computers that typically connect using a wired or wireless communications medium such as personal computers, multiprocessor systems, microprocessor-based or programmable electronic devices, network PCs, or the like. In some embodiments, client computers 102-105 may include virtually any portable computer capable of connecting to another computer and receiving information such as, laptop computer 103, mobile computer 104, tablet computers 105, or the like. However, portable computers are not so limited and may also include other portable computers such as cellular telephones, display pagers, radio frequency (RF) devices, infrared (IR) devices, Personal Digital Assistants (PDAs), handheld computers, wearable computers, integrated devices combining one or more of the preceding computers, or the like. As such, client computers 102-105 typically range widely in terms of capabilities and features. Moreover, client computers 102-105 may access various computing applications, including a browser, or other web-based application.

A web-enabled client computer may include a browser application that is configured to receive and to send web pages, web-based messages, and the like. The browser application may be configured to receive and display graphics, text, multimedia, and the like, employing virtually any web-based language, including a wireless application protocol messages (WAP), and the like. In one embodiment, the browser application is enabled to employ Handheld Device Markup Language (HDML), Wireless Markup Language (WML), WMLScript, JavaScript, Standard Generalized Markup Language (SGML), HyperText Markup Language (HTML), eXtensible Markup Language (XML), JavaScript Object Notation (JSON), or the like, to display and send a message. In one embodiment, a user of the client computer may employ the browser application to perform various activities over a network (online). However, another application may also be used to perform various online activities.

Client computers 102-105 also may include at least one other client application that is configured to receive and/or send content between another computer. The client application may include a capability to send and/or receive content, or the like. The client application may further provide information that identifies itself, including a type, capability, name, and the like. In one embodiment, client computers 102-105 may uniquely identify themselves through any of a variety of mechanisms, including an Internet Protocol (IP) address, a phone number, Mobile Identification Number (MIN), an electronic serial number (ESN), universally unique identifiers (UUIDs), or other device identifiers. Such information may be provided in a network packet, or the like, sent between other client computers, machine learning model repository server computer 116, one or more source data server computers 118, or other computers.

Client computers 102-105 may further be configured to include a client application that enables an end-user to log into an end-user account that may be managed by another computer, such as machine learning model repository server computer 116, one or more source data server computers 118, or the like. Such an end-user account, in one non-limiting example, may be configured to enable the end-user to manage one or more online activities, including in one non-limiting example, project management, software development, system administration, data modeling, search activities, social networking activities, browse various websites, communicate with other users, or the like. Also, client computers may be arranged to enable users to display reports, interactive user-interfaces, and/or results provided by machine learning model repository server computer 116.

Wireless network 108 is configured to couple client computers 103-105 and its components with network 110. Wireless network 108 may include any of a variety of wireless sub-networks that may further overlay stand-alone ad-hoc networks, and the like, to provide an infrastructure-oriented connection for client computers 103-105. Such sub-networks may include mesh networks, Wireless LAN (WLAN) networks, cellular networks, and the like. In one embodiment, the system may include more than one wireless network.

Wireless network 108 may further include an autonomous system of terminals, gateways, routers, and the like connected by wireless radio links, and the like. These connectors may be configured to move freely and randomly and organize themselves arbitrarily, such that the topology of wireless network 108 may change rapidly.

Wireless network 108 may further employ a plurality of access technologies including 2nd (2G), 3rd (3G), 4th (4G) 5th (5G) generation radio access for cellular systems, WLAN, Wireless Router (WR) mesh, and the like. Access technologies such as 2G, 3G, 4G, 5G, and future access networks may enable wide area coverage for mobile computers, such as client computers 103-105 with various degrees of mobility. In one non-limiting example, wireless network 108 may enable a radio connection through a radio network access such as Global System for Mobil communication (GSM), General Packet Radio Services (GPRS), Enhanced Data GSM Environment (EDGE), code division multiple access (CDMA), time division multiple access (TDMA), Wideband Code Division Multiple Access (WCDMA), High Speed Downlink Packet Access (HS-DPA), Long Term Evolution (LTE), and the like. In essence, wireless network 108 may include virtually any wireless communication mechanism by which information may travel between client computers 103-105 and another computer, network, a cloud-based network, a cloud instance, or the like.

Network 110 is configured to couple network computers with other computers, including, machine learning model repository server computer 116, one or more source data server computers 118, client computers 102-105 through wireless network 108, or the like. Network 110 is enabled to employ any form of computer readable media for communicating information from one electronic device to another. Also, network 110 can include the Internet in addition to local area networks (LANs), wide area networks (WANs), direct connections, such as through a universal serial bus (USB) port, other forms of computer-readable media, or any combination thereof. On an interconnected set of LANs, including those based on differing architectures and protocols, a router acts as a link between LANs, enabling messages to be sent from one to another. In addition, communication links within LANs typically include twisted wire pair or coaxial cable, while communication links between networks may utilize analog telephone lines, full or fractional dedicated digital lines including T1, T2, T3, and T4, and/or other carrier mechanisms including, for example, E-carriers, Integrated Services Digital Networks (ISDNs), Digital Subscriber Lines (DSLs), wireless links including satellite links, or other communications links known to those skilled in the art. Moreover, communication links may further employ any of a variety of digital signaling technologies, including without limit, for example, DS-0, DS-1, DS-2, DS-3, DS-4, OC-3, OC-12, OC-48, or the like. Furthermore, remote computers and other related electronic devices could be remotely connected to either LANs or WANs via a modem and temporary telephone link. In one embodiment, network 110 may be configured to transport information of an Internet Protocol (IP).

Additionally, communication media typically embodies computer readable instructions, data structures, program modules, or other transport mechanism and includes any information non-transitory delivery media or transitory delivery media. By way of example, communication media includes wired media such as twisted pair, coaxial cable, fiber optics, wave guides, and other wired media and wireless media such as acoustic, RF, infrared, and other wireless media.

One embodiment of machine learning model repository server computer 116 is described in more detail below in conjunction with FIG. 3. Briefly, however, machine learning model repository server computer 116 includes virtually any network computer that is specialized to provide data modeling services as described herein.

Although FIG. 1 illustrates machine learning model repository server computer 116 as a single computer, the innovations and/or embodiments are not so limited. For example, one or more functions of machine learning model repository server computer 116, or the like, may be distributed across one or more distinct network computers. Moreover, machine learning model repository server computer 116 is not limited to a particular configuration such as the one shown in FIG. 1. Thus, in one embodiment, machine learning model repository server computer 116 may be implemented using a plurality of network computers. In other embodiments, server computers may be implemented using a plurality of network computers in a cluster architecture, a peer-to-peer architecture, or the like. Further, in at least one of the various embodiments, machine learning model repository server computer 116 may be implemented using one or more cloud instances in one or more cloud networks. Accordingly, these innovations and embodiments are not to be construed as being limited to a single environment, and other configurations, and architectures are also envisaged.

Illustrative Client Computer

Figure 2:
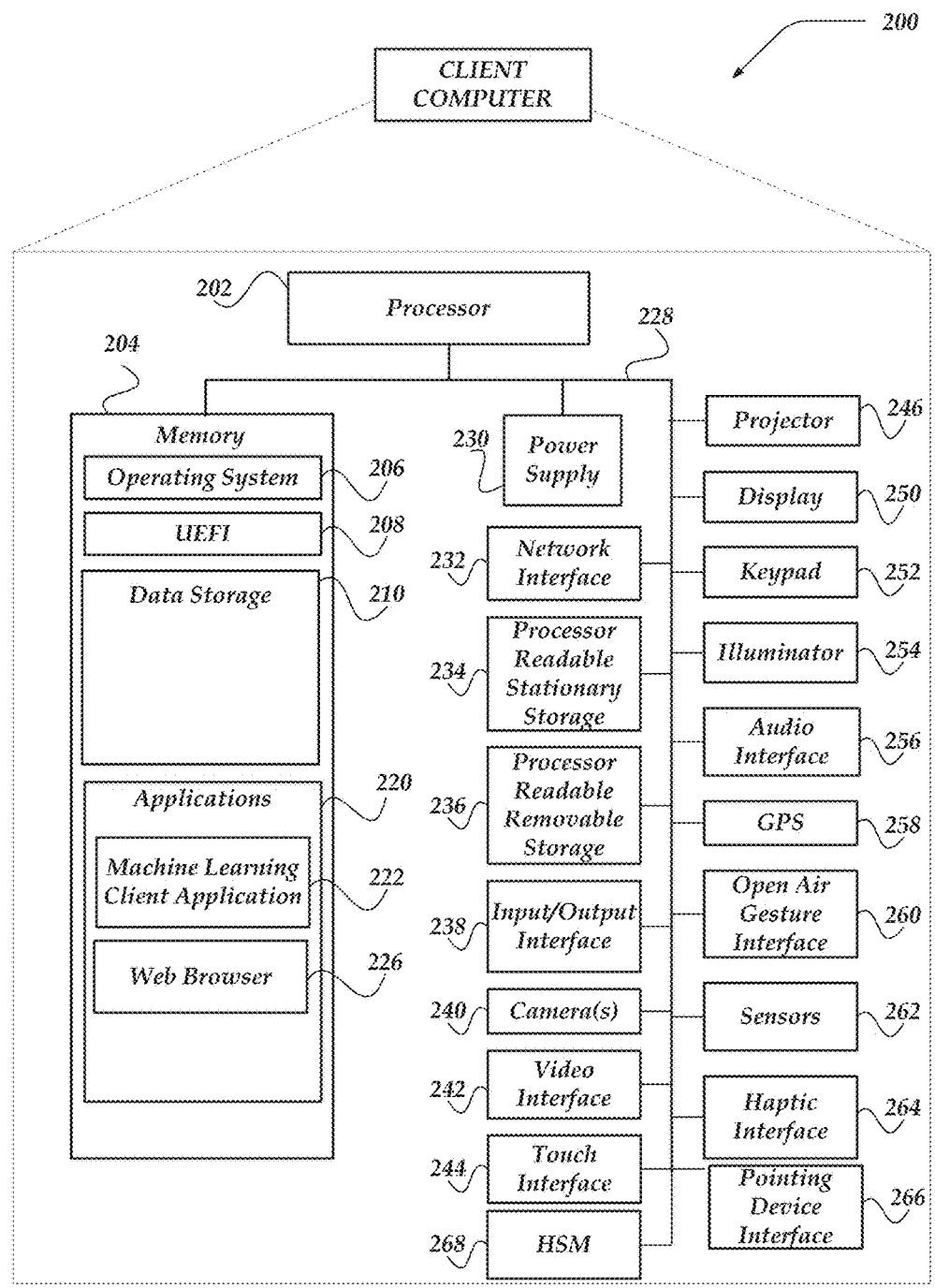
FIG. 2 shows a schematic embodiment of a client computer.

FIG. 2 shows one embodiment of client computer 200 that may include many more or less components than those shown. Client computer 200 may represent, for example, at least one embodiment of mobile computers or client computers shown in FIG. 1.

Client computer 200 may include one or more processors, such as processor 202 in communication with memory 204 via bus 228. Client computer 200 may also include power supply 230, network interface 232, audio interface 256, display 250, keypad 252, illuminator 254, video interface 242, input/output interface 238, haptic interface 264, global positioning systems (GPS) receiver 258, open air gesture interface 260, temperature interface 262, camera(s) 240, projector 246, pointing device interface 266, processor-readable stationary storage device 234, and processor-readable removable storage device 236. Client computer 200 may optionally communicate with a base station (not shown), or directly with another computer. And in one embodiment, although not shown, a gyroscope, accelerometer, or the like may be employed within client computer 200 to measuring and/or maintaining an orientation of client computer 200.

Power supply 230 may provide power to client computer 200. A rechargeable or non-rechargeable battery may be used to provide power. The power may also be provided by an external power source, such as an AC adapter or a powered docking cradle that supplements and/or recharges the battery.

Network interface 232 includes circuitry for coupling client computer 200 to one or more networks, and is constructed for use with one or more communication protocols and technologies including, but not limited to, protocols and technologies that implement any portion of the OSI model for mobile communication (GSM), CDMA, time division multiple access (TDMA), UDP, TCP/IP, SMS, MMS, GPRS, WAP, UWB, WiMax, SIP/RTP, GPRS, EDGE, WCDMA, LTE, UMTS, OFDM, CDMA2000, EV-DO, HSDPA, or any of a variety of other wireless communication protocols. Network interface 232 is sometimes known as a transceiver, transceiving device, or network interface card (NIC).

Audio interface 256 may be arranged to produce and receive audio signals such as the sound of a human voice. For example, audio interface 256 may be coupled to a speaker and microphone (not shown) to enable telecommunication with others and/or generate an audio acknowledgement for some action. A microphone in audio interface 256 can also be used for input to or control of client computer 200, e.g., using voice recognition, detecting touch based on sound, and the like.

Display 250 may be a liquid crystal display (LCD), gas plasma, electronic ink, electronic paper, light emitting diode (LED), Organic LED (OLED) or any other type of light reflective or light transmissive display that can be used with a computer. Display 250 may also include a touch interface 244 arranged to receive input from an object such as a stylus or a digit from a human hand, and may use resistive, capacitive, surface acoustic wave (SAW), infrared, radar, or other technologies to sense touch and/or gestures.

Projector 246 may be a remote handheld projector or an integrated projector that is capable of projecting an image on a remote wall or any other reflective object such as a remote screen.

Video interface 242 may be arranged to capture video images, such as a still photo, a video segment, an infrared video, or the like. For example, video interface 242 may be coupled to a digital video camera, a web-camera, or the like. Video interface 242 may comprise a lens, an image sensor, and other electronics. Image sensors may include a complementary metal-oxide-semiconductor (CMOS) integrated circuit, charge-coupled device (CCD), or any other integrated circuit for sensing light.

Keypad 252 may comprise any input device arranged to receive input from a user. For example, keypad 252 may include a push button numeric dial, or a keyboard. Keypad 252 may also include command buttons that are associated with selecting and sending images.

Illuminator 254 may provide a status indication and/or provide light. Illuminator 254 may remain active for specific periods of time or in response to events. For example, when illuminator 254 is active, it may backlight the buttons on keypad 252 and stay on while the client computer is powered. Also, illuminator 254 may backlight these buttons in various patterns when particular actions are performed, such as dialing another client computer. Illuminator 254 may also cause light sources positioned within a transparent or translucent case of the client computer to illuminate in response to actions.

Further, client computer 200 may also comprise hardware security module (HSM) 268 for providing additional tamper resistant safeguards for generating, storing and/or using security/cryptographic information such as, keys, digital certificates, passwords, passphrases, two-factor authentication information, or the like. In some embodiments, hardware security module may be employed to support one or more standard public key infrastructures (PKI), and may be employed to generate, manage, and/or store keys pairs, or the like. In some embodiments, HSM 268 may be arranged as a hardware card that may be added to a client computer.

Client computer 200 may also comprise input/output interface 238 for communicating with external peripheral devices or other computers such as other client computers and network computers. The peripheral devices may include an audio headset, display screen glasses, remote speaker system, remote speaker and microphone system, and the like. Input/output interface 238 can utilize one or more technologies, such as Universal Serial Bus (USB), Infrared, WiFi, WiMax, Bluetooth™, Bluetooth Low Energy. or the like.

Haptic interface 264 may be arranged to provide tactile feedback to a user of the client computer. For example, the haptic interface 264 may be employed to vibrate client computer 200 in a particular way when another user of a computer is calling. Open air gesture interface 260 may sense physical gestures of a user of client computer 200, for example, by using single or stereo video cameras, radar, a gyroscopic sensor inside a computer held or worn by the user, or the like. Camera 240 may be used to track physical eye movements of a user of client computer 200.

In at least one of the various embodiments, client computer 200 may also include sensors 262 for determining geolocation information (e.g., GPS), monitoring electrical power conditions (e.g., voltage sensors, current sensors, frequency sensors, and so on), monitoring weather (e.g., thermostats, barometers, anemometers, humidity detectors, precipitation scales, or the like), light monitoring, audio monitoring, motion sensors, or the like. Sensors 262 may be one or more hardware sensors that collect and/or measure data that is external to client computer 200

GPS transceiver 258 can determine the physical coordinates of client computer 200 on the surface of the Earth, which typically outputs a location as latitude and longitude values. GPS transceiver 258 can also employ other geo-positioning mechanisms, including, but not limited to, triangulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or the like, to further determine the physical location of client computer 200 on the surface of the Earth. It is understood that under different conditions, GPS transceiver 258 can determine a physical location for client computer 200. In at least one embodiment, however, client computer 200 may, through other components, provide other information that may be employed to determine a physical location of the client computer, including for example, a Media Access Control (MAC) address, IP address, and the like.

In at least one of the various embodiments, applications, such as, machine learning client application 222, web browser 226, or the like, may be arranged to employ geo-location information to select one or more localization features, such as, time zones, languages, currencies, calendar formatting, or the like. Localization features may be used in user-interfaces, reports, as well as internal processes and/or databases. In at least one of the various embodiments, geo-location information used for selecting localization information may be provided by GPS 258. Also, in some embodiments, geolocation information may include information provided using one or more geolocation protocols over the networks, such as, wireless network 108 and/or network 111.

Human interface components can be peripheral devices that are physically separate from client computer 200, allowing for remote input and/or output to client computer 200. For example, information routed as described here through human interface components such as display 250 or keyboard 252 can instead be routed through network interface 232 to appropriate human interface components located remotely. Examples of human interface peripheral components that may be remote include, but are not limited to, audio devices, pointing devices, keypads, displays, cameras, projectors, and the like. These peripheral components may communicate over a Pico Network such as Bluetooth™, Zigbee™, Bluetooth Low Energy, or the like. One non-limiting example of a client computer with such peripheral human interface components is a wearable computer, which might include a remote pico projector along with one or more cameras that remotely communicate with a separately located client computer to sense a user's gestures toward portions of an image projected by the pico projector onto a reflected surface such as a wall or the user's hand.

A client computer may include web browser application 226 that may be configured to receive and to send web pages, web-based messages, graphics, text, multimedia, and the like. The client computer's browser application may employ virtually any programming language, including a wireless application protocol messages (WAP), and the like. In at least one embodiment, the browser application is enabled to employ Handheld Device Markup Language (HDML), Wireless Markup Language (WML), WMLScript, JavaScript, Standard Generalized Markup Language (SGML), HyperText Markup Language (HTML), eXtensible Markup Language (XML), HTML5, and the like.

Memory 204 may include RAM, ROM, and/or other types of memory. Memory 204 illustrates an example of computer-readable storage media (devices) for storage of information such as computer-readable instructions, data structures, program modules or other data. Memory 204 may store Unified Extensible Firmware Interface (UEFI) 208 for controlling low-level operation of client computer 200. The memory may also store operating system 206 for controlling the operation of client computer 200. It will be appreciated that this component may include a general-purpose operating system such as a version of UNIX, or LINUX™, or a specialized client computer communication operating system such as Windows Phone™. The operating system may include, or interface with a Java and/or JavaScript virtual machine modules that enable control of hardware components and/or operating system operations via Java application programs or JavaScript programs.

Memory 204 may further include one or more data storage 210, which can be utilized by client computer 200 to store, among other things, applications 220 and/or other data. For example, data storage 210 may also be employed to store information that describes various capabilities of client computer 200. The information may then be provided to another device or computer based on any of a variety of events, including being sent as part of a header during a communication, sent upon request, or the like. Data storage 210 may also be employed to store social networking information including address books, buddy lists, aliases, user profile information, user credentials, or the like. Data storage 210 may further include program code, data, algorithms, and the like, for use by a processor, such as processor 202 to execute and perform actions. In one embodiment, at least some of data storage 210 might also be stored on another component of client computer 200, including, but not limited to, non-transitory processor-readable removable storage device 236, processor-readable stationary storage device 234, or even external to the client computer.

Applications 220 may include computer executable instructions which, when executed by client computer 200, transmit, receive, and/or otherwise process instructions and data. Applications 220 may include, for example, machine learning client application 222, web browser 226, or the like. In at least one of the various embodiments, machine learning client application 222 may be used to interact with a machine learning model repository.

Other examples of application programs include calendars, search programs, email client applications, IM applications, SMS applications, Voice Over Internet Protocol (VOIP) applications, contact managers, task managers, transcoders, database programs, word processing programs, security applications, spreadsheet programs, games, search programs, and so forth.

Additionally, in one or more embodiments (not shown in the figures), client computer 200 may include one or more embedded logic hardware devices instead of one or more CPUs, such as, an Application Specific Integrated Circuits (ASICs), Field Programmable Gate Arrays (FPGAs), Programmable Array Logic (PAL), or the like, or combination thereof. The embedded logic hardware devices may directly execute embedded logic to perform actions. Also, in one or more embodiments (not shown in the figures), the client computer may include one or more hardware microcontrollers instead of one or more CPUs. In at least one embodiment, the microcontrollers be system-on-a-chips (SOCs) that may directly execute their own embedded logic to perform actions and access their own internal memory and their own external Input and Output Interfaces (e.g., hardware pins and/or wireless transceivers) to perform actions.

Illustrative Network Computer

Figure 3:
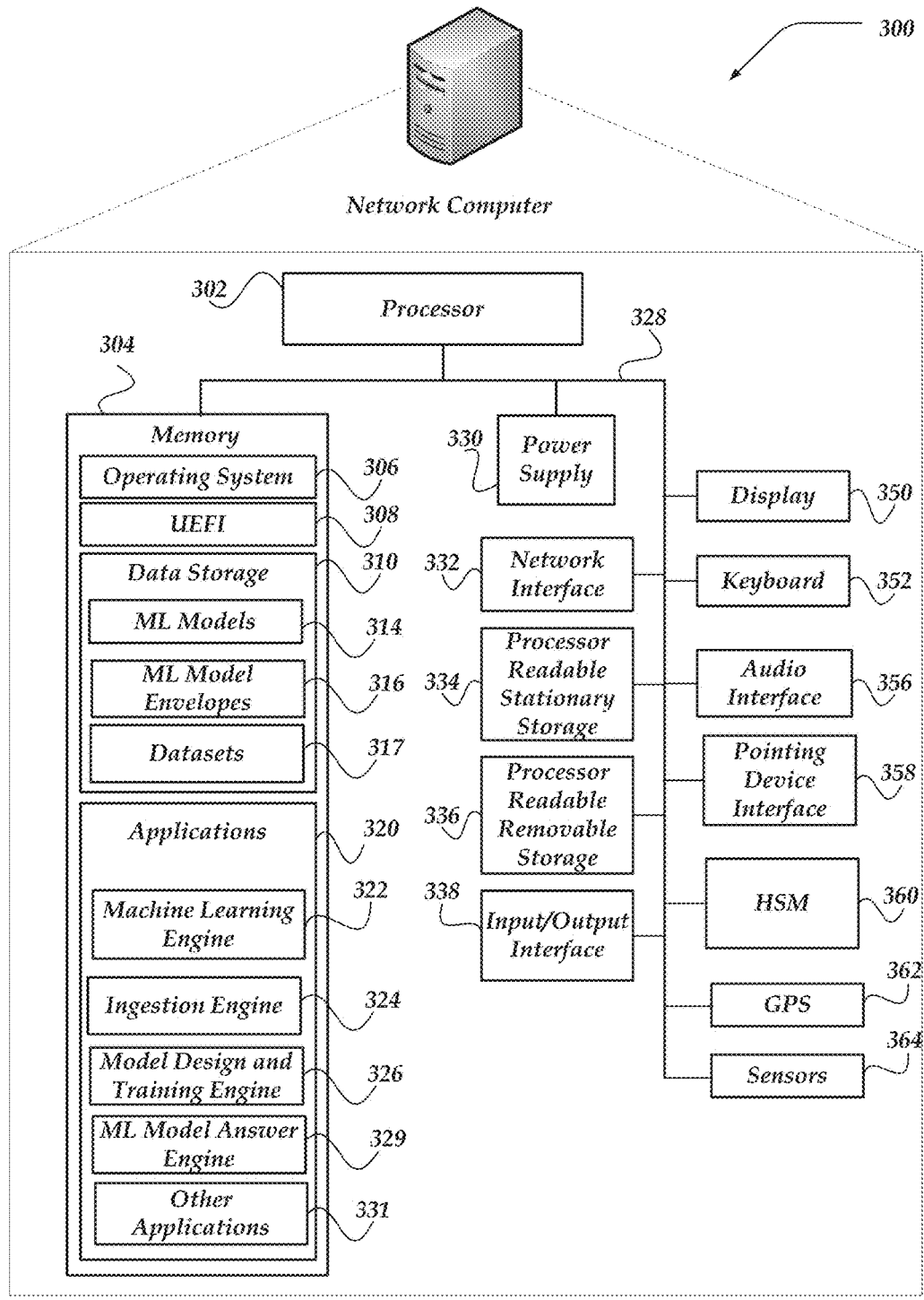
FIG. 3 illustrates a schematic embodiment of a network computer.

FIG. 3 shows one embodiment of network computer 300 that may be included in a system implementing one or more embodiments of the described innovations. Network computer 300 may include many more or less components than those shown in FIG. 3. However, the components shown are sufficient to disclose an illustrative embodiment for practicing these innovations. Network computer 300 may represent, for example, one embodiment of machine learning model repository server computer 116 of FIG. 1.

As shown in the figure, network computer 300 includes a processor 302 in communication with a memory 304 via a bus 328. Network computer 300 also includes a power supply 330, network interface 332, audio interface 356, global positioning systems (GPS) receiver 362, display 350, keyboard 352, input/output interface 338, processor-readable stationary storage device 334, and processor-readable removable storage device 336. Power supply 330 provides power to network computer 300. In some embodiments, processor 302 may be a multiprocessor system that includes one or more processors each having one or more processing/execution cores.

Network interface 332 includes circuitry for coupling network computer 300 to one or more networks, and is constructed for use with one or more communication protocols and technologies including, but not limited to, protocols and technologies that implement any portion of the Open Systems Interconnection model (OSI model), global system for mobile communication (GSM), code division multiple access (CDMA), time division multiple access (TDMA), user datagram protocol (UDP), transmission control protocol/Internet protocol (TCP/IP), Short Message Service (SMS), Multimedia Messaging Service (MMS), general packet radio service (GPRS), WAP, ultra wide band (UWB), IEEE 802.16 Worldwide Interoperability for Microwave Access (WiMax), Session Initiation Protocol/Realtime Transport Protocol (SIP/RTP), or any of a variety of other wired and wireless communication protocols. Network interface 332 is sometimes known as a transceiver, transceiving device, or network interface card (NIC). Network computer 300 may optionally communicate with a base station (not shown), or directly with another computer.

Audio interface 356 is arranged to produce and receive audio signals such as the sound of a human voice. For example, audio interface 356 may be coupled to a speaker and microphone (not shown) to enable telecommunication with others and/or generate an audio acknowledgement for some action. A microphone in audio interface 356 can also be used for input to or control of network computer 300, for example, using voice recognition.

Display 350 may be a liquid crystal display (LCD), gas plasma, electronic ink, light emitting diode (LED), Organic LED (OLED) or any other type of light reflective or light transmissive display that can be used with a computer. Display 350 may be a handheld projector or pico projector capable of projecting an image on a wall or other object.

Network computer 300 may also comprise input/output interface 338 for communicating with external devices or computers not shown in FIG. 3. Input/output interface 338 can utilize one or more wired or wireless communication technologies, such as USB™, Firewire™, WiFi, WiMax, Thunderbolt™, Infrared, Bluetooth™, Zigbee™, serial port, parallel port, and the like.

GPS transceiver 362 can determine the physical coordinates of network computer 300 on the surface of the Earth, which typically outputs a location as latitude and longitude values. GPS transceiver 362 can also employ other geo-positioning mechanisms, including, but not limited to, triangulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or the like, to further determine the physical location of network computer 300 on the surface of the Earth. It is understood that under different conditions, GPS transceiver 362 can determine a physical location for network computer 300.

Network computer 300 may also include sensors 364 for determining geolocation information (e.g., GPS), monitoring electrical power conditions (e.g., voltage sensors, current sensors, frequency sensors, and so on), monitoring weather (e.g., thermostats, barometers, anemometers, humidity detectors, precipitation scales, or the like), light monitoring, audio monitoring, motion sensors, or the like. Sensors 364 may be one or more hardware sensors that collect and/or measure data that is external to network computer 300

In at least one embodiment, however, network computer 300 may, through other components, provide other information that may be employed to determine a physical location of the client computer, including for example, a Media Access Control (MAC) address, IP address, and the like.

Human interface components can be physically separate from network computer 300, allowing for remote input and/or output to network computer 300. For example, information routed as described here through human interface components such as display 350 or keyboard 352 can instead be routed through the network interface 332 to appropriate human interface components located elsewhere on the network. Human interface components include any component that allows the computer to take input from, or send output to, a human user of a computer. Accordingly, pointing devices such as mice, styluses, track balls, or the like, may communicate through pointing device interface 358 to receive user input.

Memory 304 may include Random Access Memory (RAM), Read-Only Memory (ROM), and/or other types of non-transitory computer readable and/or writeable media. Memory 304 illustrates an example of computer-readable storage media (devices) for storage of information such as computer-readable instructions, data structures, program modules or other data. Memory 304 stores a unified extensible firmware interface (UEFI) 308 for controlling low-level operation of network computer 300. The memory also stores an operating system 306 for controlling the operation of network computer 300. It will be appreciated that this component may include a general-purpose operating system such as a version of UNIX, or LINUX™, or a specialized operating system such as Microsoft Corporation's Windows® operating system, or the Apple Corporation's OSX® operating system. The operating system may include, or interface with a Java virtual machine module that enables control of hardware components and/or operating system operations via Java application programs. Likewise, other runtime environments may be included.

Memory 304 may further include one or more data storage 310, which can be utilized by network computer 300 to store, among other things, applications 320 and/or other data. For example, data storage 310 may also be employed to store information that describes various capabilities of network computer 300. The information may then be provided to another device or computer based on any of a variety of events, including being sent as part of a header during a communication, sent upon request, or the like. Data storage 410 may also be employed to store social networking information including address books, buddy lists, aliases, user profile information, or the like. Data storage 310 may further include program code, data, algorithms, and the like, for use by one or more processors, such as processor 302 to execute and perform actions such as those actions described below. In one embodiment, at least some of data storage 310 might also be stored on another component of network computer 300, including, but not limited to, non-transitory media inside processor-readable removable storage device 336, processor-readable stationary storage device 334, or any other computer-readable storage device within network computer 300, or even external to network computer 300. Data storage 310 may include, for example, machine learning (ML) models 314, ML model envelopes 316, datasets 317 (e.g., customer data set, validation data sets, training data sets, or the like), or the like.

Applications 320 may include computer executable instructions which, when executed by network computer 300, transmit, receive, and/or otherwise process messages (e.g., SMS, Multimedia Messaging Service (MMS), Instant Message (IM), email, and/or other messages), audio, video, and enable telecommunication with another user of another mobile computer. Other examples of application programs include calendars, search programs, email client applications, IM applications, SMS applications, Voice Over Internet Protocol (VOIP) applications, contact managers, task managers, transcoders, database programs, word processing programs, security applications, spreadsheet programs, games, search programs, and so forth. Applications 320 may include machine learning (ML) engine 322, ingestion engine 324, ML model training engine 326, ML model answer engine 329, other applications 331, or the like, that may perform actions further described below. In at least one of the various embodiments, one or more of the applications may be implemented as modules and/or components of another application. Further, in at least one of the various embodiments, applications may be implemented as operating system extensions, modules, plugins, or the like.

In at least one of the various embodiments, applications, such as, machine learning (ML) engine 322, ingestion engine 324, ML model training engine 326, ML model answer engine 32, other applications 331, or the like, may be arranged to employ geo-location information to select one or more localization features, such as, time zones, languages, currencies, calendar formatting, or the like. Localization features may be used in user-interfaces, reports, as well as internal processes and/or databases. In at least one of the various embodiments, geo-location information used for selecting localization information may be provided by GPS 362. Also, in some embodiments, geolocation information may include information provided using one or more geo-location protocols over the networks, such as, wireless network 108 and/or network 110.

Furthermore, in at least one of the various embodiments, machine learning (ML) engine 322, ingestion engine 324, ML model training engine 326, ML model answer engine 329, other applications 331, may be operative in a cloud-based computing environment. In at least one of the various embodiments, these engines, and others, that comprise the machine learning model repository that may be executing within virtual machines and/or virtual servers that may be managed in a cloud-based based computing environment. In at least one of the various embodiments, in this context applications including the engines may flow from one physical network computer within the cloud-based environment to another depending on performance and scaling considerations automatically managed by the cloud computing environment. Likewise, in at least one of the various embodiments, virtual machines and/or virtual servers dedicated to machine learning (ML) engine 322, ingestion engine 324, ML model training engine 326, ML model answer engine 329, other applications 331, may be provisioned and de-commissioned automatically.

Further, in some embodiments, network computer 300 may also include hardware security module (HSM) 360 for providing additional tamper resistant safeguards for generating, storing and/or using security/cryptographic information such as, keys, digital certificates, passwords, passphrases, two-factor authentication information, or the like. In some embodiments, hardware security module may be employ to support one or more standard public key infrastructures (PKI), and may be employed to generate, manage, and/or store keys pairs, or the like. In some embodiments, HSM 360 may be arranged as a hardware card that may be installed in a network computer.

Additionally, in one or more embodiments (not shown in the figures), network computer 300 may include an one or more embedded logic hardware devices instead of one or more CPUs, such as, Application Specific Integrated Circuits (ASICs), Field Programmable Gate Arrays (FPGAs), Programmable Array Logic (PALs), or the like, or combination thereof. The one or more embedded logic hardware devices may directly execute its embedded logic to perform actions. Also, in one or more embodiments (not shown in the figures), the network computer may include one or more hardware microcontrollers instead of one or more CPUs. In at least one embodiment, the one or more microcontrollers may directly execute embedded logic to perform actions and access their own internal memory and their own external Input and Output Interfaces (e.g., hardware pins and/or wireless transceivers) to perform actions. E.g., they may be arranged as Systems On Chips (SOCs).

Illustrative Logical System Architecture

Figure 4:
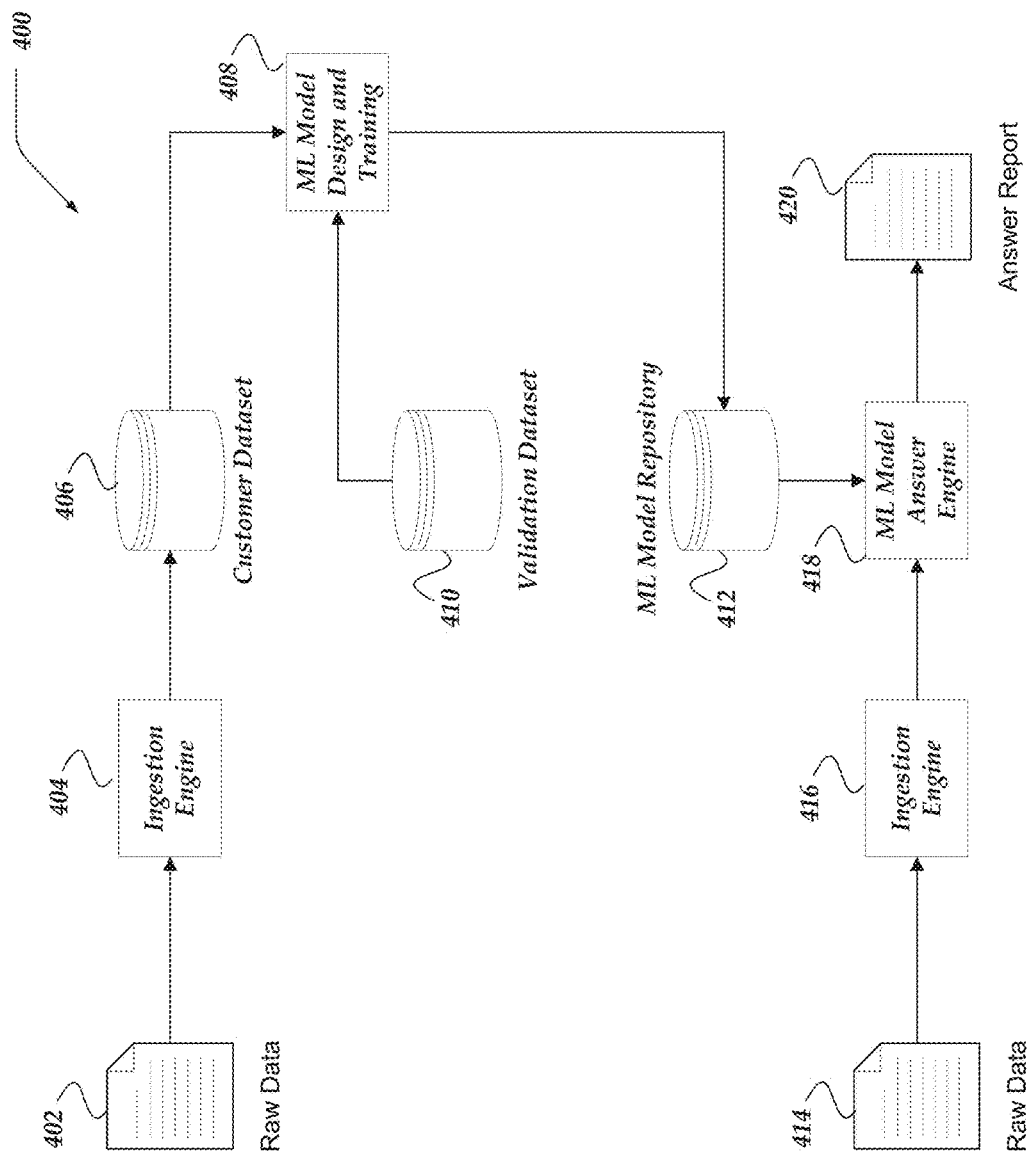
FIG. 4 shows a logical schematic of a portion of a machine learning model repository system arranged in accordance with one or more of the various embodiments.

FIG. 4 shows a logical schematic of a portion of machine learning model repository system 400 arranged in accordance with one or more of the various embodiments. In one or more of the various embodiments, system 400 represents logical interaction between or among machine learning (ML) engine 322, ingestion engine 324, ML model training engine 326, ML model answer engine 329, or the like, that may be hosted by one or more network computers, such as, as network computer 300.

In one or more of the various embodiments, system 400 may be arranged to include one or more raw data sets, such as, raw data 402 comprising a customer data from various sources. In this example, raw data 402 represents customer data that has been previously collected by a customer. In some cases, raw data 402 may include historical data collected from various sources.

In one or more of the various embodiments, raw data 402 may be provided to an ingestion engine, such as, ingestion engine 404. In one or more of the various embodiments, ingestion engine 404 may be arranged to execute one or more data ingestion processes to pre-processors some or all of raw data 404 to provide objects that are compatible with the ML model repository, For example, ingestion engine 404 may be arranged to conform raw data to a well-defined schema used by the ML model repository platform.

In one or more of the various embodiments, customer dataset 406 represents customer objects that conform to an defined schema (e.g., model schema). In one or more of the various embodiments, customer data set 406 may be one or more data stores, such as, databases, cloud-based storage, file stores, or the like. In some embodiments, some or all of customer data set 406 may be distributed across different locations. Likewise, in some embodiments, the contents of data set 406 may be segregated into various priority tiers such as, local caches, distributed caches, normal storage, archival storage, or the like. In one or more of the various embodiments, the data segregation may occur during ingestion based on the execution of one or more ingestion rules, or it may occur later sometime after the data is initially ingested.

In one or more of the various embodiments, machine learning (ML) model design and training engine 408 may be arranged to employ customer data set 406 to enable customer/users to design, implements, train, or test various machine learning models. ML model design and training engine may include one or more user interfaces that enable users, such as, data scientists, to design, validate, or train ML models. In one or more of the various embodiments, if a ML model is trained it may be added to a ML model repository data store, such as ML model repository 412. Accordingly, in some embodiments, it may then be made available to classify or otherwise provide answers based on information provided by the customer or other applications.

Also, in one or more of the various embodiments, ML Models may be designed or trained based on one or more validation data sets that may be made available by the ML modeling platform. For example, in some embodiments, validation dataset 410 may include various data sets that are arranged to conform to one or more model schemas supported by the ML modeling platform. Accordingly, in one or more of the various embodiments, customers may be enabled to design and train ML models using the provided validation datasets rather than having to provide their own data for training their ML Models.

In one or more of the various embodiments, ML models stored in ML model repository 412 may be made available to one or more users or customers for use with their own data inputs. In some embodiments, the customers or users may be enabled to employ one or more ML models that may have been provided by other users and shared or otherwise made available.

In one or more of the various embodiments, raw data 414 represents production data provided by a customer. In one or more of the various embodiments, raw data 414 may be similar to raw data 402. In some cases, raw data 402 and raw data 414 may contain the same information or overlapping information. In some embodiments raw data 414 may be other data collected separately or subsequently from raw data 402. In some embodiments, raw data 414 may be produced or collected according one or more well-defined schedules. Likewise, raw data 414 may include streaming data or real-time data.

In one or more of the various embodiments, production raw data, such as, raw data 411 still may require ingestion. Accordingly, in some embodiments, an ingestion engine, such as, ingestion engine 416 may be arranged to convert raw data 414 to model objects that conform to the appropriate model schema. Next, in one or more of the various embodiments, those model objects may be provided to a ML model answer engine, such as, ML model answer engine 418 that may be arranged to provide model object to one or more ML models from repository 412. Accordingly, in one or more of the various embodiments, ML model answer engine 418 may be arranged to provide one or more answer reports, such as, answer report 420 that include one or more answers provided by ML model answer engine 418.

Figure 5:
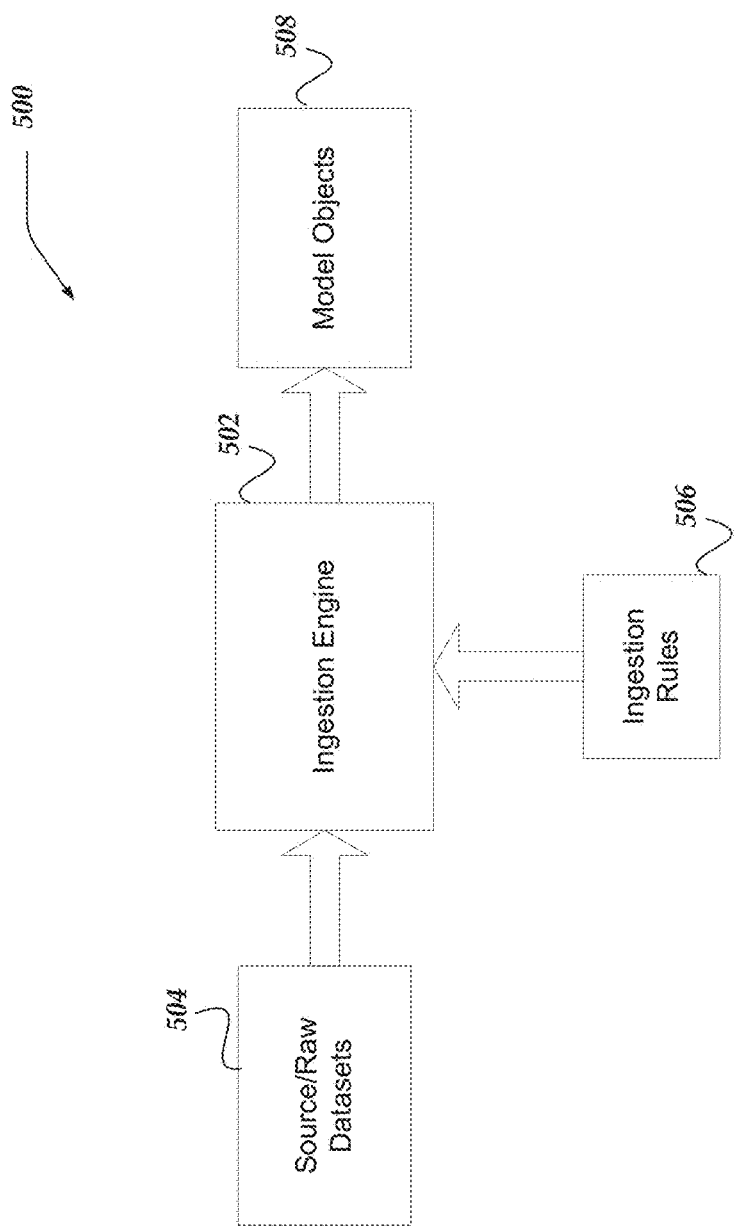
FIG. 5 illustrates a logical system for ingesting customer data sets in accordance with one or more the various embodiments.

FIG. 5 illustrates logical system 500 for ingesting customer data sets in accordance with one or more the various embodiments. In at least one of the various embodiments, system 500 may include: an ingestion engine, such as, ingestion engine 502; one or more raw data sets, such as, raw data set 504; ingestion rules, such as, ingestion rules 506; or the like. In at least one of the various embodiments, ingestion engine 502 may employ raw data set 504, and ingestion rules 506 to provide model objects 508.

In at least one of the various embodiments, model objects 508 may represent objects that have been coerced into objects the conform with a modeling schema supported by the machine learning modeling platform.

In at least one of the various embodiments, model objects may be normalized such that anomalies, such as, spelling errors, divergent abbreviations and/or short hand notations, different values representation the same concept, may be "normalized" to common values/representations defined by the modeling schema.

In some embodiments, ingestion rules 506 may include rules and information for mapping various ad hoc/colloquial/casual names that may be used for the raw data values to a common names or data types supported by the modeling schema. For example, depending on the source of the raw data, different names or values may be entered into the data for same modeling schema field. For example, in some cases, the raw data values may be represented using abbreviations, in other cases, the raw data may be spelled using different/various capitalization, spelling, and so on. Accordingly, in at least one of the various embodiments, ingestion engine 502 may be arranged to execute one or more ingestion rules to map from one or more values in the raw datasets to a value that may be consistent with the modeling schema.

Likewise, in one or more of the various embodiments, ingestion engine 502 may be arranged to map one or more properties in the raw datasets to particular fields of particular model objects based on the modeling schema.

In one or more of the various embodiments, raw data sets, such as, raw data sets 504 may be provided by one or more source data server computers, such as, source data server computer 118. Accordingly, in some embodiments, source data servers may communicate notifications over a network to indicate that raw data is available for ingestion. In some cases, if network communication with the between the machine learning model repository servers and source data servers may be inactive or otherwise disabled, the raw data may be cached at the source data server. Thus, if the communication between the source data servers and the machine learning model repository servers is enabled again, the source data servers may communicate a notification indicating that the network communication (e.g., a network connection) has been re-established. Also, when the network connection is re-established, the ingestion engine may be arranged to obtain any cached or remaining raw data records from one or more source data servers.

Also, in at least one of the various embodiments, a notification may be provided from another source, including a user. Such notifications may indicate that one or more raw data sets have changed and/or one or more raw data sets are available for ingestion. Accordingly, in at least one of the various embodiments, when the ingestion engine establishes network communication with the one or more source data servers it may, in acknowledgement of the notifications, obtain the updated raw data for ingestion.

In at least one of the various embodiments, ingestion rules may include one or more sets of instructions/conditions for transforming raw data records into model data records. In at least one of the various embodiments, the ingestion rules may be arranged to normalize values includes in raw data records to the values that comprise the model data records. Normalizing in this context can mean to map/transform various input values to common values, and the like, rather than being limited to arithmetical normalization.

In at least one of the various embodiments, ingestion rules 506 may be arranged to compare raw data values with values in the allowed or expected values based on the modeling schema. In at least one of the various embodiments, one or more rules may include patterning matching instructions that may compare values in the raw data records with expected value.

Also, in at least one of the various embodiments, ingestion rules 506 may be arranged to scan more than one field in the raw records to determine a correct mapping/transformation for model objects. In some embodiments, there may be information scattered across different fields/columns of the raw data records that may be viewed as a whole to make a determination for a mapping/transformation to a model object.

In at least one of the various embodiments, one or more of the ingestion rules may be arranged based on prior knowledge of the structure and/or fields of the raw datasets. Accordingly, one or more fields of the raw datasets records may be used for mapping directly to a field of the model object. For example, in at least one of the various embodiments, if raw data records may include a field labeled 'LastName' that is known to include the last name of an employee, the ingestion rule may be arranged to directly map the LastName fields to the last name field of the employee model object.

Continuing with the same non-limiting example, in other embodiments, in the absence of prior knowledge, the ingestion rules may be arranged to scan raw data records to look for contents that appear to be an employee's last name and then map those values into a model object's last name field.

In one or more of the various embodiments, raw datasets 504 may be provided in bulk as part of an initial on-boarding of customer. For example, initial preparation for a new customer may include ingesting customer raw datasets into a ML modeling repository. Likewise, in some embodiments, raw datasets (e.g., raw data) may be provided periodically or real-time as it is collected by the customer. For example, in some embodiments, if the customer is a health clinic, raw data such as patient intake information may be provided as patients are seen by the clinic. In some embodiments, such data may be collected and provided periodically (e.g., every hour, daily, or the like) or it may be provided in real-time as patients as encountered.

In one or more of the various embodiments, raw datasets 504 may be databases or other data stores maintained by the customer. In other embodiments, raw datasets 504 may be provided via direct or indirect integration with other third party systems of services, such as, for example, patient intake applications, hospital management applications, insurance companies, or the like. Further, in some embodiments, one or more users may be enabled to directly provide (e.g., data entry) data to an ingestion engine.

Figure 6:
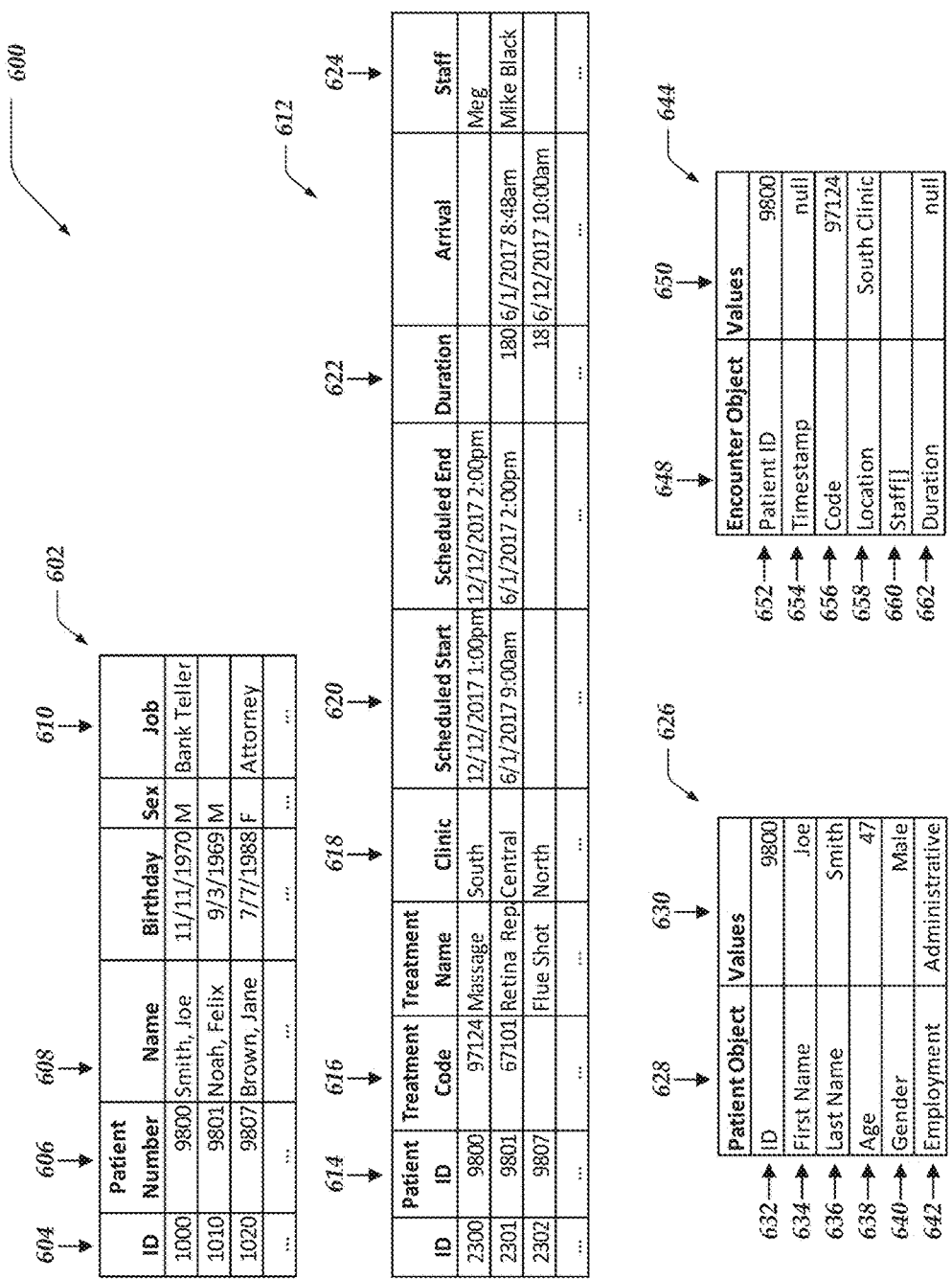
FIG. 6 illustrates a logical system for ingesting data sets in accordance with one or more the various embodiments.

FIG. 6 illustrates logical system 600 for ingesting data sets in accordance with one or more the various embodiments. In this example, system 600 represent portions of a raw data set and portions of model objects produced therefrom by an ingestion engine.

Accordingly, in at least one of the various embodiments, system 600 may include: patient raw data 602, appointment raw data 612, patient model object 626, and encounter object 644.

In this example, patient raw data 602, represent a raw data representation of a patient of a healthcare enterprise. In this example, for some embodiments, patient raw data 602 includes, row ID column 604, patient number column 606, name column 608, job column 610, among others. Also, in this example, appointment raw data 612 may be arranged to include, various columns, such as, patient ID 614, treatment code 616, clinic 618, duration 622, staff 624, or the like.

In one or more of the various embodiments, the raw data objects (e.g., patient raw data 602 and appointment raw data 612) may be provided to an ingestion engine. Accordingly, in some embodiments, the ingestion engine may be arranged to provide one or more model objects, such as, patient object 626 and encounter object 644, based on the raw data objects and one or more ingestion rules.

In one or more of the various embodiments, the ingestion engine may be arranged to execute one or more ingestion rules that transform raw data into model objects that conform to one or more defined model schemas.

In this example, patient object 626 is represents using fields 628 and field values 630. In some embodiments, patient objects, such as patient object 626 may include fields, such as ID field 632, first name field 634, last name field 636, age 638, gender 640, employment 642, or the like. Likewise, in this example, encounter object 644 represents a patient's encounter with a healthcare enterprise. Accordingly, for this example, it include encounter object fields 648 and encounter object field values 650. Further, in this example, encounter object 644 may be arranged to include fields, such as, patient ID field 652, timestamp field 654, code field 656, location field 658, staff field 660, duration field 662, or the like.

In some embodiments, the ingestion engine may be arranged take raw data objects and produce models objects.

In this example, patient data 602 is arranged to include the patient's first name and last name in one field (e.g., column 608). However, the patient model object require first name and last name to be separate fields. Accordingly, in this example, for some embodiments, the ingestion engine may be arranged to execute an ingestion rule that parse the name column values of patient raw data objects to extract the first name and last name so they may be values for the first name field and last name field of patient model objects. In one or more of the various embodiments, additional transformations may be required, such as, converting raw data birthdate values include age field values, and so on.

Figure 7:
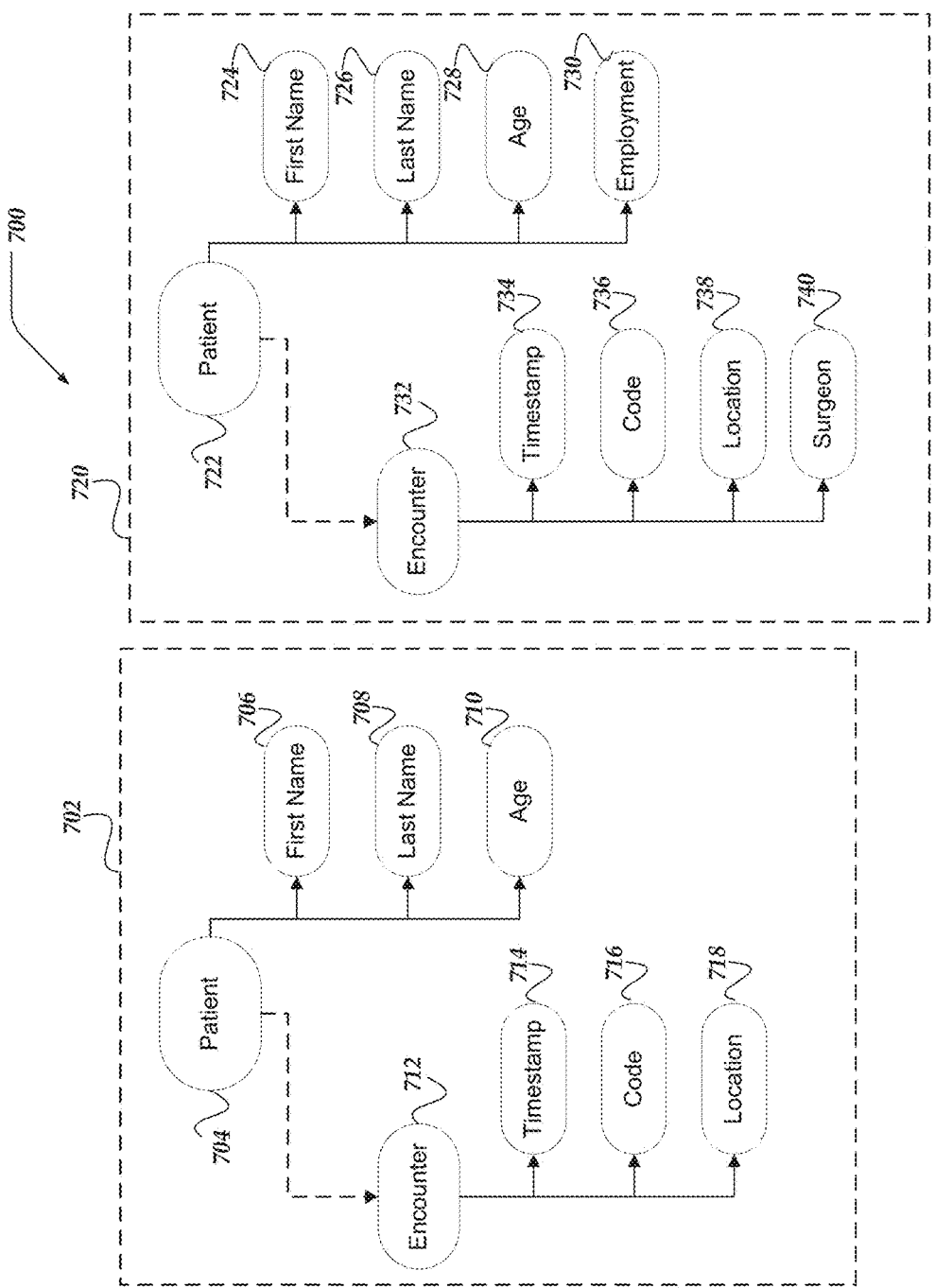
FIG. 7 illustrates a logical system for representing model objects in accordance with one or more the various embodiments.

FIG. 7 illustrates logical system 700 for representing data models that include model objects in accordance with one or more the various embodiments. In this example, system 700 represent portions data models that include model objects created from ingested raw data sets. In one or more of the various embodiments, the ML model repository may be arranged to include one or more model schemas that may be represented as one or more graphs. Accordingly, in one or more of the various embodiments, model objects may be included in data models represented as graphs where populated field values in the model objects may be the nodes (e.g., vertices) and the relationship between the field and the model object or other model object are represented by the edges of the graph.

In one or more of the various embodiments, each model object and its data model representation may be restricted or constrained such that they conform to the model schema. In one or more of the various embodiments, model objects may be arranged such that they may include fewer fields than the model schema allows. Accordingly, in some embodiments, model objects may be arranged to include as much information that may be available for a given object.

In one or more of the various embodiments, some instances of model objects may be missing information while other instances have fields that represent information missing for other model objects. In one or more of the various embodiments, the variation between different instances of model objects may be related to various factors, such as, raw data variability, raw data errors, sampling or data collection time differences, or the like.

As discussed above, in one or more of the various embodiments, during ingestion, the ingestion engine may transform fields from raw data objects into model object fields that conform with the model schema. However, in one or more of the various embodiments, if the field information is unavailable to the ingestion engine, it may produce a model object that may be based on the available information. For example, if patient raw data omits a patient's first name, the patient model object may be created and added to the customer dataset absent a first name field. However, in one or more of the various embodiments, if missing field data is provided later, the appropriate model object fields may be added to the model object and their including data model may be modified accordingly. Note, in some embodiments, information may be missing by design or on account of errors.

For example, in one or more of the various embodiments, raw data patient object 602 includes three patients, two of those raw data patients include an entry for Job and one does not. Accordingly, in this example, patient model objects corresponding to those three patient raw data objects may be processed such that two patient model objects will have their employment field populated while the one patient model object that corresponds to the raw data patient missing the Job fields may be created absent a value of employment.

Thus, in one or more of the various embodiments, some definitions in the model schema may be permissive in the sense that some missing fields may be allowed. However, in some embodiments, the model schema may be arranged to prevent unknown or new fields being added to a model object. In some embodiments, the ingestion engine may be arranged to apply one or more ingestion rules to provide default or placeholder values for a given model object field.

In one or more of the various embodiments, as instances of model objects are provided by an ingestion engine, the ingestion engine may be arranged to generate a data model that has graph corresponding to the model objects.

In this example, data model 702 represents patient model object 704 and encounter object 712. In some embodiments, patient model object 704 may include one or more fields such as first name field 706, last name field 708, and age field 710.

Similarly, in this example, data model 720 represents another patient model object instance, patient model object 722. In this example, patient model object 722 represents an instance that includes first name field 706, last name field 708, age field 728, and employment field 730.

Note, in this example, there are two patient model objects that (are assumed to) conform to the same model schema. However, in this example, for one or more of the various embodiments, since patient model object 702 does not have a value for employment field, that the employment field may be omitted from its data model. In some embodiments, the underlying data structure used to implement model objects or data models may be arranged to maintain a placeholder for all the potential fields for a given model object type. Alternatively, in some embodiments, the fields may be added as needed if they are allowed by the model schema.

In one or more of the various embodiments, model schemas may also define one or more relationships between different model objects. In this example, patient object 704 is related to encounter object 712 (indicated here by an edge illustrated with a dotted line) and patient object 722 is related to 732. In this example, the relationship represents that an encounter object represents an encounter with a particular patient. Accordingly, in this example, encounter object 712, includes timestamp field 714, code field 716, and location field 718. Likewise, in this example, encounter object 732 includes timestamp field 734, code field 736, location field 738, and surgeon field 740.

In this example, the flexibility of the model schema is illustrated by encounter object 732 including surgeon field 740 that represents a surgeon that was involved with the encounter. In contrast, in this example, encounter object 712 does not include a surgeon field. In this example, encounter object 712 does not include surgeon field because its associated raw data object did not include this information.

Note, in one or more of the various embodiments, model object generation depends on the interplay of the raw data objects and the ingestion rules. In this example, ingestion rules may be arranged to interpret values for code field 736 based on the Treatment Code column 616 in raw data appointment object 612. In this example, the appointment associated with patient ID 9081 (the second record from the top of appointment object 612) includes a treatment code that corresponds to a surgery and it also includes a staff member listed as Mike Black (column 624). Thus, for example, the ingestion engine may be arranged to assume the staff member listed for a surgery is a surgeon. Also, in some embodiments, ingestion engines may be arranged to perform various validation operations to confirm inferences. For example, in this example, the ingestion engine may be arranged to confirm that "Mike Black" is listed in a table of known surgeons that are associated with a the treatment code/code for a given appointment.

As discussed above, in one or more of the various embodiments, raw data used to provide model objects may come from different sources at different times. For example, in some embodiments, patient raw data may be collected every hour while appointment raw data may be collected every four hours. Thus, in this example, one or more patient model objects may be provided absent one or more relevant encounter objects (e.g., model objects representing patient appointments) because the raw data for patients may be provided before the raw data for encounters is available.

As relevant model objects become available via ingestion they may be added to the data model the includes the model objects. In some embodiments, in this example, edges that represent relationships between different model objects will be added to the data models as the model objects become available. In this example, the edges between patient model objects, such as patient model object 704, and encounter model objects, such as encounter model object 712 are represented using the dashed line because it may be absent if the patient model object or the encounter model object have not been ingested.

Figure 8A:
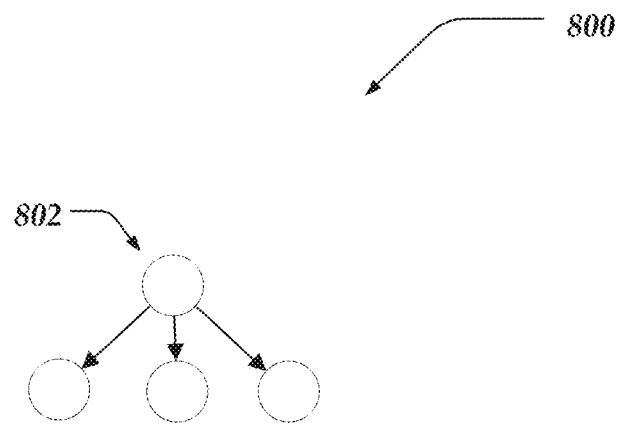
FIG. 8A illustrates a first model object being added to a data model in accordance with one or more the various embodiments.
Figure 8B:
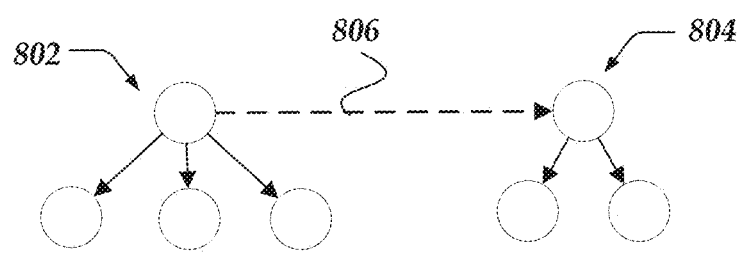
FIG. 8B illustrates a second model object being added to a data model and associated with another model object via a relationship edge in accordance with one or more the various embodiments.

FIGS. 8A and 8B illustrate logical system 800 for representing model objects and data models in accordance with one or more the various embodiments. These figures illustrate how a data model that include model objects may be incrementally extended or created as the ingestion engine ingests various raw data objects to add model objects or model object fields to a system.

FIG. 8A illustrates a first model object (e.g., model object 802) is added to a data model in accordance with one or more the various embodiments. For example, this could be a patient model object. Initially it is added to the data model. Note, any given model object may be comprised fields that may be of various data types, including, single values, lists, sets, ranges, other model objects, or the like.

FIG. 8B illustrates how an second model object, model object 804 is added to a data model associated with model object 802 via relationship edge 806 in accordance with one or more the various embodiments. In one or more of the various embodiments, the ingestion engine may be arranged to recognize relationships based on the model schema. For example, the ingestion engine may be arranged to map values from raw data object into particular fields of model objects. Thus, in some embodiments, the model schema may be arranged to define allowed relationships between model objects based on defined key field values. For examples, the model schema may be arranged to define a relationship between patient objects and encounter objects based on them sharing the same value for patient ID, or the like. Thus, in some embodiments, as model objects are added to a data model the relationships that conform to the model schema may be included.

Figure 9:
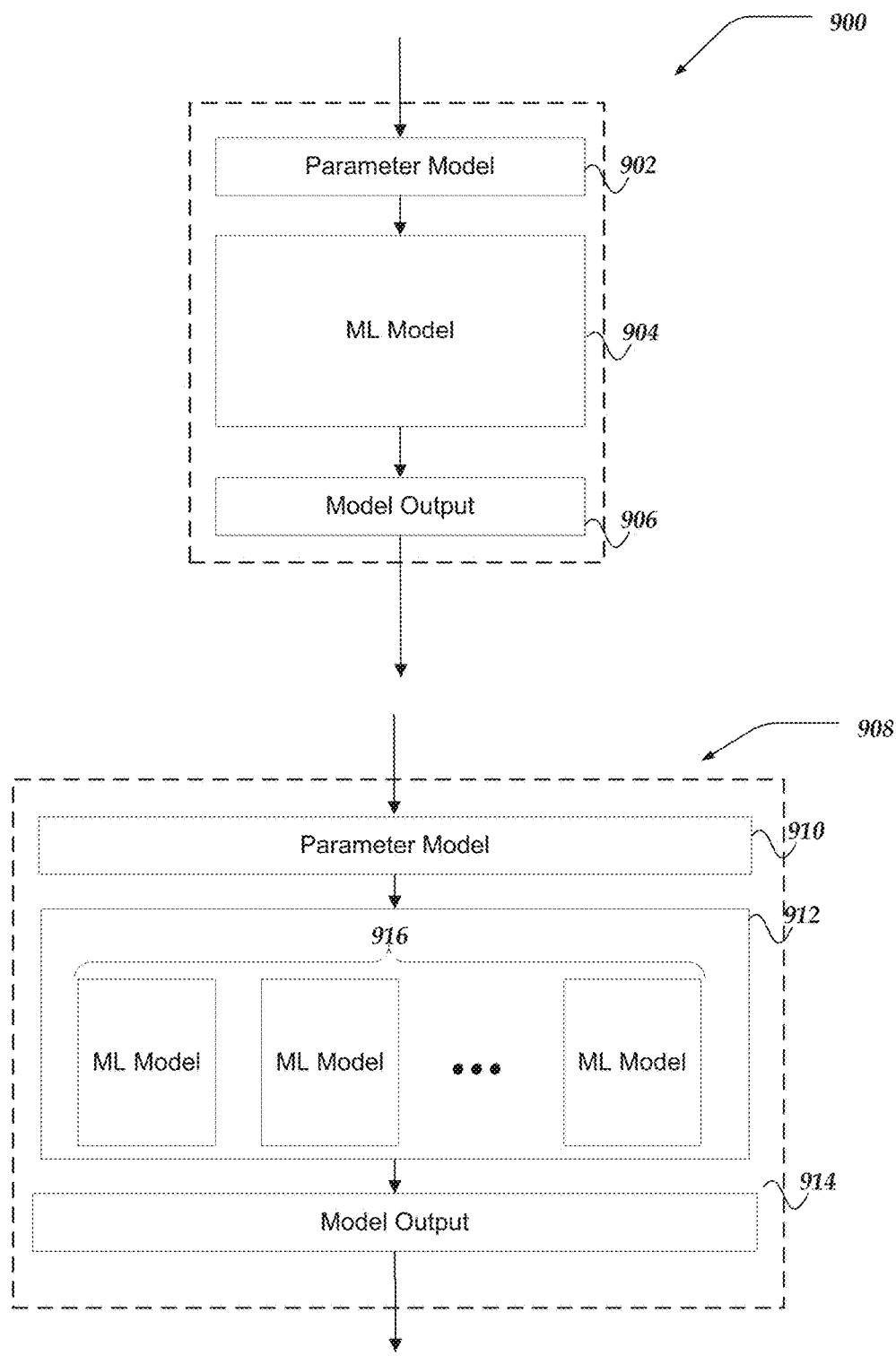
FIG. 9 illustrates logical representation of a machine learning (ML) model envelope for scoring model objects in accordance with one or more the various embodiments.

FIG. 9 illustrates logical representation of machine learning (ML) model envelope 900 for scoring model objects in accordance with one or more the various embodiments. In one or more of the various embodiments, ML model envelopes may be comprised of parameter model 902, ML model 904, model output 906, or the like.

In one or more of the various embodiments, a parameter model, such as parameter model 902 may be defined in terms of the model schema. In some embodiments, parameter model 902 may act as a guard that restricts which model objects may be provided to a ML model or ML model envelope. In one or more of the various embodiments, parameter model 902 may identify one or more portions of a data model that may be provided to a particular ML model, such as ML model 904.

In one or more of the various embodiments, parameter models define the model objects that are applicable or eligible for scoring with a given ML model or ML model envelope. For example, in one or more of the various embodiments, parameter model 902 may be arranged to require model objects that conform to a data model portion such as data model 702. While, in some embodiments, different parameter models may be arranged to accept different model objects, such as data model 720. Note, in one or more of the various embodiments, a ML model that can consume data model 702 may also be able to consume data model 720 since data model 720 includes all of the required model objects and fields to meet such a requirement. However, a ML model that requires data model 720 would exclude data model 702 since data model 702 is missing one or more required model objects or model object fields, such as, in this example, where a surgeon field in the encounter model object and employment field in the patient model object may be required by a parameter model.

In one or more of the various embodiments, ML model 904 represents the actual machine learning model included in ML model envelope 900 that may be executed by the machine learning engine. In some embodiments, a machine learning repository or ML model answer engine may be arranged to provide one or more model objects that match a ML model envelope's parameter model. Accordingly, the ML model may accept the matching model objects that satisfy the parameter model and produce a score based on the provided model objects.

In one or more of the various embodiments, the particular ML model or its underlying model implementation may be arbitrary as long as it accepts the model objects that satisfy its associated parameter model. For example, a simple ML model may be arranged to provide scores that indicates if a patient is old or young. Accordingly, in this example, the ML model may include parameter model that requires a patient model object that includes an age value. Thus, in this trivial example, the ML model may be arranged to produce a true result if the age value is above a defined threshold. In contrast, in some embodiments, ML models may be arranged to be a complex artificial neural network that is trained to consume data models that include several complex model objects have many model object fields.

In one or more of the various embodiments, parameter model 902 may be used by a ML model answer engine, such as ML model answer engine 329, to query the customer dataset for model objects that may be eligible inputs to a given ML model or ML model envelopes. For example, if the parameter model requires patients that have one or more encounters with health facility, model objects conforming to data model 702 or data model 720 would be eligible. However, in some embodiments, if the parameter model for a ML model require patient model objects that include employment information and encounter model objects that are associated with surgeons and surgery, model objects conforming to data model 720 would be eligible for scoring.

In one or more of the various embodiments, ML models may be comprised of two or more other ML models. For example, ML model envelope 908 includes ML model 912 that is comprised of two or more ML models (e.g., ML models 916). Accordingly, in one or more of the various embodiments, parameter model 910 may be arranged to accept model objects conforming to data models that are required or compatible with the included ML models 916. Likewise, in one or more of the various embodiments, model object 914 may be arranged to produce output values based on a combination of sub-outputs produced by ML model 916. Note, the particular combination of the sub-outputs may be included as part of ML model 912 or model output 914 based on the application of ML model 912. In some embodiments, ML models that include more than one ML model may be arranged include rules that select one or more sub-outputs to include or combine into its ultimate output. For example, in some embodiments, ML model 912 may be arranged to exclude one or more outlying results and then provide a score that is based on an average of the remaining results. Likewise, in some embodiments, rules may employ dynamic programming such that one or more of the included ML models are used depending on the input parameter values.

Also, in one or more of the various embodiments, one or more ML models may be arranged in series or in parallel. In some embodiments, one or more ML models may be arranged to score model objects before they are provided to other ML models for additional scoring. In some embodiments, one or more ML models may be employed as a filter to select model objects to pass to other ML models for further scoring. For example, a first ML model may be used to score objects such that model objects associated with a score the is outside a defined range of values may be excluded from consideration of the one or more other included ML models.

In one or more of the various embodiments, the specific application of the included ML models, such as ML models 916 may be determined during the model training phase. For example, if the included ML models are employed as portions of an artificial neural network that is trained as a whole, the details of learned models, such as, connection weights, cost function parameters, or the like, may be determined based on model training rather than intentional design.

Generalized Operations

FIGS. 10-14 represent the generalized operations for a machine learning model repository in accordance with at least one of the various embodiments. In one or more of the various embodiments, processes 1000, 1100, 1200, 1300, and 1400 described in conjunction with FIGS. 10-14 may be implemented by and/or executed on a single network computer, such as network computer 300 of FIG. 3. In other embodiments, these processes or portions thereof may be implemented by and/or executed on a plurality of network computers, such as network computer 300 of FIG. 3. However, embodiments are not so limited, and various combinations of network computers, client computers, virtual machines, or the like may be utilized. Further, one or more of the various embodiments, the processes described in conjunction with FIGS. 10-14 may be operative in a machine learning model repository such as described in conjunction with FIGS. 4-9.

Figure 10:
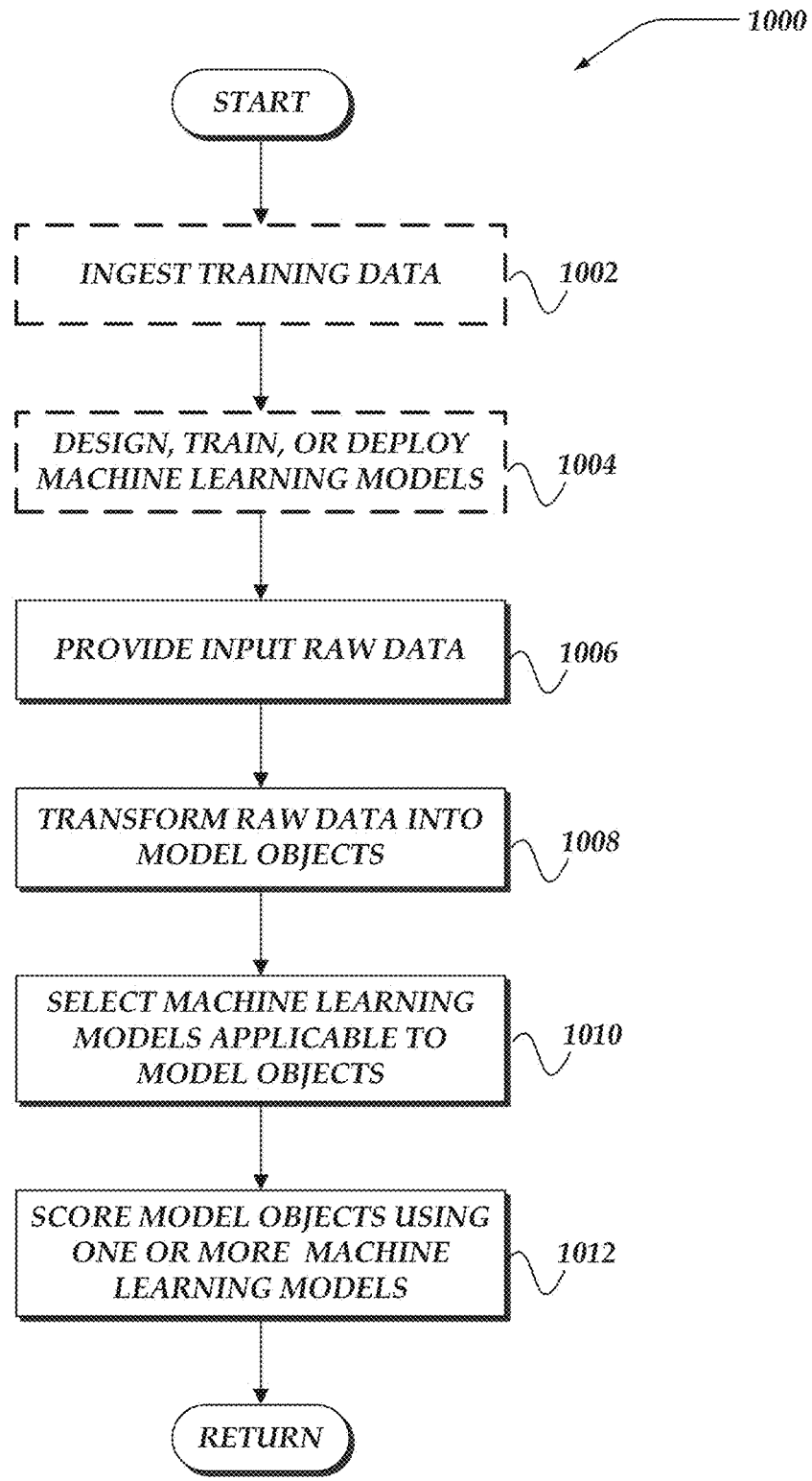
FIG. 10 illustrates an overview flowchart for a process for a machine learning (ML) repository in accordance with one or more of the various embodiments.

FIG. 10 illustrates an overview flowchart for process 1000 for a machine learning (ML) repository in accordance with one or more of the various embodiments. After a start block, at block 1002, in one or more of the various embodiments, optionally, a ML learning repository may be arranged ingest training data. As described above, customer may be enabled to provide training data based on their own raw data sets. Accordingly, in one or more of the various embodiments, the ingesting engine may ingest the raw data and transform it as necessary to conform it two one or more model schemas that may be supported or enforced by the ML model repository.

This block is indicated as being optional, because in some embodiments, a customer may be enabled to use training data sets that are already available in the ML model repository. For example, the repository may be loaded with validation data sets that include model objects sufficient for training ML models. In some cases, the model objects may be have been provided based on a customer's raw data that was ingested earlier. In other cases, for some embodiments, the model objects used by a customer for training may be provided by third-party data providers.

At block 1004, in one or more of the various embodiments, optionally, the customer (e.g., a user of the ML model repository) may be enabled to design, train, or deploy one or more ML models and include them in one or more ML model envelopes. As described above, a user may design one or more ML models based on the available model objects or model schema.

In one or more of the various embodiments, designing ML models may include providing one or more queries, evaluators, expression, rules, conditions, seed values, or the like, that will comprise the ML model. In one or more of the various embodiments, one or more portions of the ML models may be designed using programs, scripts, data structures, or the like, using one or more computer programming languages, such as, R, Matlab, SAS, Perl, C++, Java, or the like, or combination thereof. Further, in some embodiments, custom programming languages may be used as well as visual programming tools or environments.

This block is indicated as being optional, because in some embodiments, a customer may be enabled to use ML models that are already available in the ML model repository. For example, the repository may be loaded with ML models sufficient for answering questions that the customer intends to propose. In some cases, the ML models may have been designed, trained, or deployed by the customer. In other cases, for some embodiments, the ML models used by a customer may be provided by third-party ML model providers. Accordingly, in some embodiments, a customer may be enabled to design ML model envelopes that include previously designed or trained ML models.

At block 1006, in one or more of the various embodiments, the ML model repository may be arranged to provide the raw input to one or more ML models. In one or more of the various embodiments, the ML model repository may be arranged to accept raw data for scoring from various sources depending on the application. In some embodiments, the raw data may be real-time data or signal feeds from other applications. In other embodiments, the raw data may be loaded periodically from one or more data stores, such as, file dumps, log files, databases, message queues, or the like.

In one or more of the various embodiments, the ML model repository may be arranged enable data from various sources to be provided. In some embodiments, the ML model repository may be arranged to have one or more ingestion interfaces that may be used to enable customers or other third-parties to provide raw data objects. For example, customers may be enabled to employ REST APIs to provide input raw data. In other embodiments, the ML model repository (e.g., the ingestion engine) may be arranged to monitor one or more data stores (e.g., file repositories, cloud-storage data repositories, or the like) and input raw data that a customer may place within.

At block 1008, in one or more of the various embodiments, the ML model repository may be arranged to transform the input raw data objects into model objects that conform with one or more model schemas. As discussed above, ML models included in the ML model repository are arranged to require model objects that conform to a particular model schema. Accordingly, in one or more of the various embodiments, an ingestion engine may be arranged to perform the necessary data processing or transformations.

At block 1010, in one or more of the various embodiments, the ML model repository may be arranged to select one or more ML models that may be applicable to the model objects produced from the raw data. In one or more of the various embodiments, the ML model repository may identify or select the one or more ML models based on a comparison of the provided model objects and the parameter models associated with each ML model. In some embodiments, ML models that are associated with a parameter model that matches the provided model objects may be selected to score the model objects.

At block 1012, in one or more of the various embodiments, the ML model repository may be arranged to score the model objects using one or more machine learning models. As described above, one or more ML models included in a ML model envelope that may be arranged to produce scores (e.g., answers or other results) based on evaluating model objects that may comprise portions of data models that conform to one or more model schemas. That particular score or result depends on the design of the ML models and the model objects that it scores. Next, control may be returned to a calling process.

Figure 11:
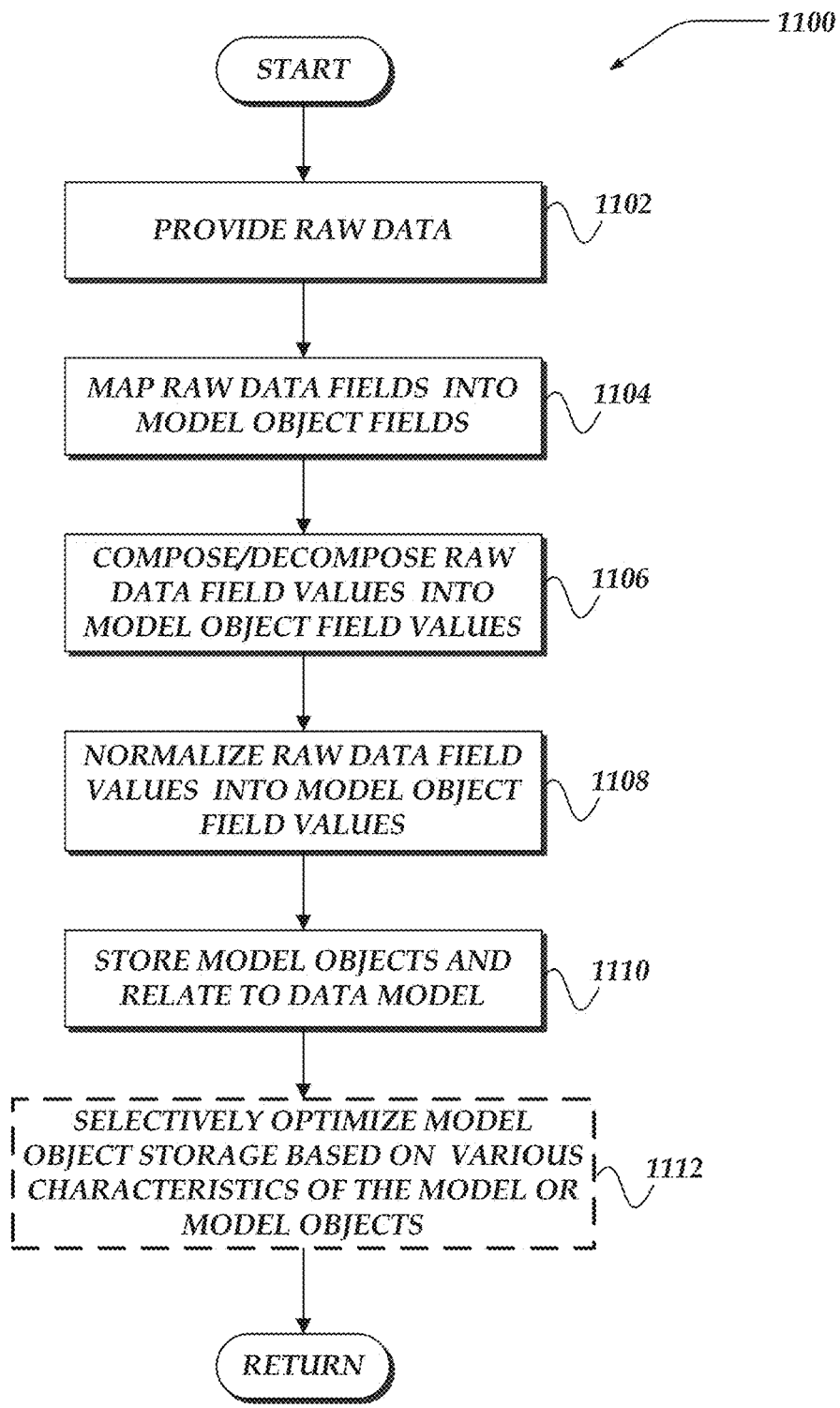
FIG. 11 illustrates a flowchart for a process for data ingestion for a machine learning (ML) repository in accordance with one or more of the various embodiments.

FIG. 11 illustrates a flowchart for process 1100 for data ingestion for a machine learning (ML) repository in accordance with one or more of the various embodiments. After a start block, at block 1102, in one or more of the various embodiments, raw data or raw data objects may be provided to an ingestion engine. As described above, the raw data may be provided in various formats or from various sources.

At block 1104, in one or more of the various embodiments, the ingestion engine may be arranged to map raw data fields into one or more model object fields. In one or more of the various embodiments, one or more raw data fields may be mapped directly to one or more model object fields. In one or more of the various embodiments, one or more ingestion rules may be executed by the ingestion engine to perform the mapping from raw data object fields to model object fields.

At block 1106, in one or more of the various embodiments, the ingestion engine may be arranged to compose or decompose one or more raw data fields into one or more model object fields. For example, if a single raw data field includes data for two model object fields, the ingestion engine may be arranged to execute one or more ingestion rules that parse the single raw data field to identify the values that should be mapped to the each of the two model object fields. Likewise, for example, if two or more raw data fields include values that together represent a single model object fields, the ingestion engine may be arranged to produce a value for the single model object field based on the two or more raw data object fields.

At block 1108, in one or more of the various embodiments, the ingestion engine may be arranged to normalize one or more raw data fields into model object field values. In one or more of the various embodiments, the ingestion engine may be arranged to execute one or more normalization operations to conform the ingested data to the model schema. For example, the model schema may constrain one or more model object fields to be represented as values from 0.0 to 1.0.

In other embodiments, a model schema may constrain model object field values in a various ways, such as, value ceilings, value floors, significant figures, rounding, fixed precision, units, set membership, sign/absolute values, data types (e.g., integers, floating points, strings), data structures (e.g., vectors, sets, sequences, multi-valued structures, or the like), value ranges, or the like, or combination thereof. Accordingly, in one or more of the various embodiments, this normalization block is not limited to classical arithmetic normalization operations, rather it is a normalization of data based on the execution of one or more ingestion rules by the ingestion engine to conform the raw data field values to the definitions or constraints required by the targeted model schema.

At block 1110, in one or more of the various embodiments, the ingestion engine may be arranged to store the model objects and relate them the data model. In one or more of the various embodiments, the ingestion engine may be arranged to traverse the model schema to identify other model objects that may be examined to see if they are related to other model objects. For example, if a model object is a patient model object, the ingestion engine may traverse the model schema and identify the encounter model objects may be related to patient objects. Accordingly, in this example, the ingestion engine may identify patient objects and encounter objects that should be related to each other. In some embodiments, if such objects are discovered, their relationship may be recorded or indicated as necessary.

At block 1112, in one or more of the various embodiments, optionally, the ML model repository may be arranged to selectively optimize model object storage or data model storage representation based on various characteristics.

In one or more of the various embodiments, while data models may normally be represented using graph models, storage may be modified or arranged to optimize performance or storage size. In one or more of the various embodiments, the ML model repository may be arranged to monitor various usage metrics, such as, frequency of use, number of model objects in query results, size of model objects, data type of model objects (e.g., text, video, images, voice audio, music audio, or the like), age of data, or the like, or combination thereof, Accordingly, In one or more of the various embodiments, the ML model repository may be arranged to execute one or more optimization policies driven by one or more optimization rules that may take into account the monitored metrics, data store characteristics, expenses, customer service plans, or the like. In some embodiments, one or more optimization policies may operate automatically. In other embodiments, optimization policies may be manually applied or applied after customer or operator approval.

In one or more of the various embodiments, optimizations may include providing additional indices, storing some model object in databases, storing some model objects on fast data stores, or the like, or combination thereof. This block is indicated as optional, because in one or more of the various embodiments, ML model repositories may be arranged to omit or defer additional optimization operations. Next, control may be returned to a calling process.

Figure 12:
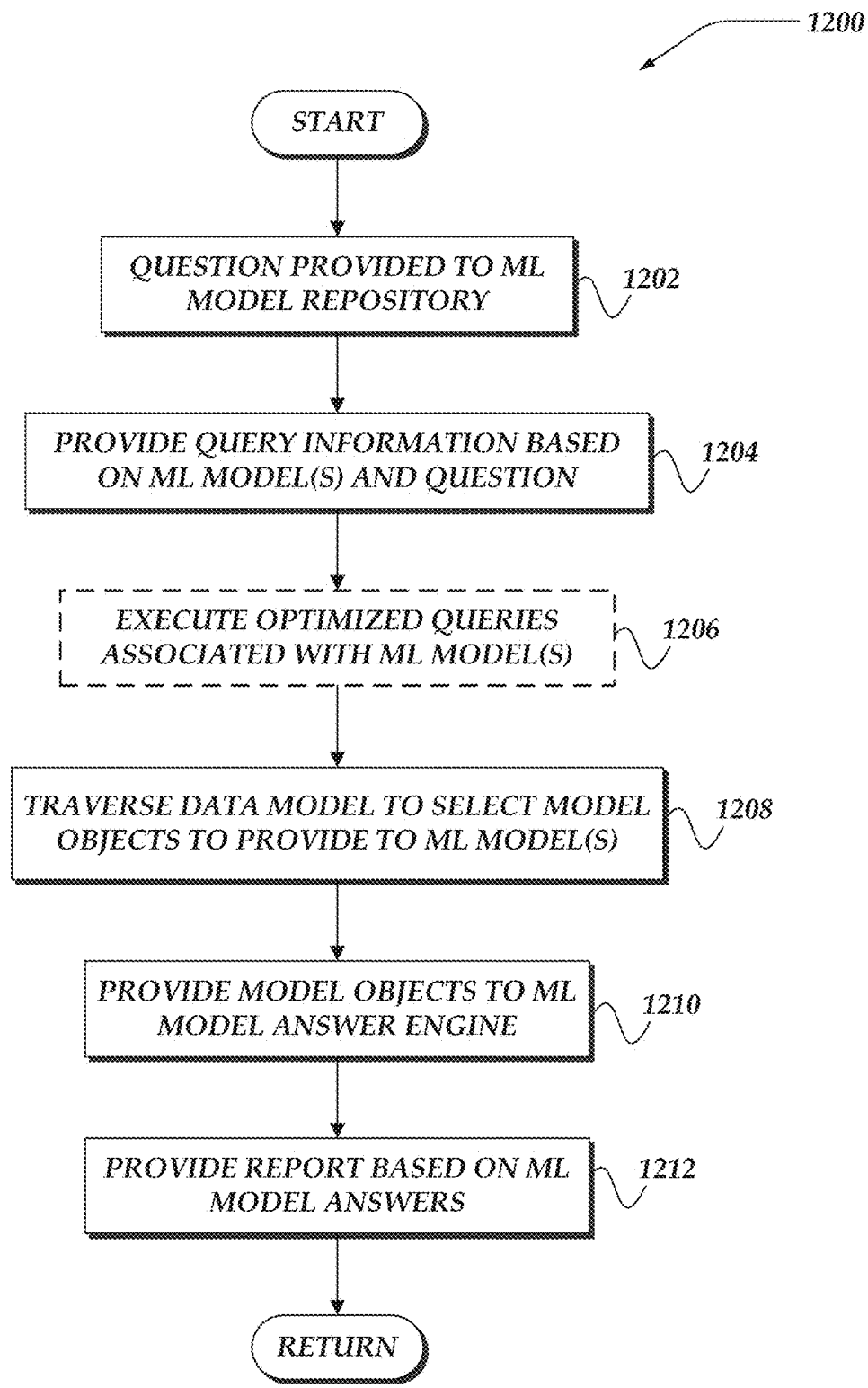
FIG. 12 illustrates a flowchart for a process for employing a machine learning (ML) repository to answer questions in accordance with one or more of the various embodiments.

FIG. 12 illustrates a flowchart for process 1200 for employing a machine learning (ML) repository to answer questions in accordance with one or more of the various embodiments. After a start block, at block 1202, in one or more of the various embodiments, one or more questions may be provided to a ML model repository. In one or more of the various embodiments, the questions may be in the form of one or more query expressions, or the like. In some embodiments, the question may be inferred, in the sense that one or more model objects may be provided to the ML model repository for scoring or classification by one or more selected ML models.

In one or more of the various embodiments, the ML model repository may be arranged to provide query information that may correspond to the provided questions. In some embodiments, the question may be a query or otherwise include the necessary query information for processing the question.

In one or more of the various embodiments, query information may be inferred from one or more ML models that the question may be directed towards. For example, in some embodiments, if a ML model designed and trained to classify or score patients that have two or more children under 10 years old, the query information may be arranged to select patients that have or more children under the age of 10 based on the ML models.

At block 1206, in one or more of the various embodiments, optionally, the ML answer engine may be arranged to execute one or more optimized queries associated with the one or more ML models or one or model objects implicated by the query information. For example, if the query information indicate that patient model objects associated with encounter model objects are the subject of the question, there may be one or more indices, query plans, caches, lookup tables, or the like, that have already been prepared in anticipation of fielding such queries. Accordingly, these optimized queries may be executed to select one or more model objects that may be relevant to the current question.

This block is indicated as optional because, in one or more of the various embodiments, depending on various factors, such as, the question, query, ML model repository, per customer policies, optimized queries may be unavailable, or the like, or combination thereof.

At block 1208, in one or more of the various embodiments, the ML model repository may be arranged to traverse the data model or model schema to select model objects to provide to one or more ML models for scoring that satisfy the parameter models of one or more ML models or ML model envelopes. In one or more of the various embodiments, a ML answer engine may be arranged to traverse the data model or model schema to select model objects that conform to the query information. In one or more of the various embodiments, model objects so selected will conform to the parameter model defined by the ML models employed for answering the provided question.

Likewise, in one or more model object have previously been selected or otherwise provided, the data model that includes the model objects may be traversed to compare it with parameter models of one or more ML models or ML model envelopes. Thus, in some embodiments, model objects that satisfy parameter models of one or more ML models or ML model envelopes may be selected for scoring.

At block 1210, in one or more of the various embodiments, the ML model repository may be arranged to provide selected model objects to one to more ML model answer engines, such as, ML model answer engine 329, or the like.

In one or more of the various embodiments, the ML model answer engine may be arranged to provide the data models that include the selected model objects to the one or more ML models or ML model envelopes associated with the question. In some embodiments, the ML model answer engine may be arranged to run one or more ML models included in one or more ML model envelopes. In some embodiments, the ML model answer engine may be arranged to execute one or more ML models in parallel or otherwise concurrently depending on the hosting environment, type of model, data location, ML model affinity, per customer policies or contracts, or the like.

In one or more of the various embodiments, some questions may require a single ML model that may be executed in parallel to classify the provided model objects. For example, multiple instances of a single ML model trained for predicting patient expense based on the provided model objects may be executed simultaneously on different hosts, such that each instance scores a different portion or segments of the provided model objects.

In one or more of the various embodiments, as described above, some ML model envelopes may include two or more ML models. In some cases, these included ML models may be arranged to execute in parallel as well. Accordingly, in one or more of the various embodiments, the ML model answer engine may split the execution of these ML models even though they are included in the same ML model envelope.

In one or more of the various embodiments, ML model envelopes that include more than one ML models may have one or more ML models arranged to depend on the output of one or more other ML models included in the same ML model envelope. For example, the selected model objects may first be scored using a first ML model before being scored by other ML models in the ML model envelope. Accordingly, in one or more of the various embodiments, the ML model answer engine may be arranged to consider these dependencies if selecting where or how to execute ML models. Thus, in one or more of the various embodiments, the ML model answer engine may intentionally assign two or more related or dependent ML models to be scored on the same host, cloud compute instance, or network computer. For example, in some embodiments, scoring two dependent ML models on the same host may avoid copying model objects from one host to another. For example, if the a first ML model is used to select a subset of model objects, if a dependent ML model is co-located the ML model repository performance overhead that may be associated with copying the selected subset of model objects to another host for additional scoring by other ML models may be eliminated.

In some embodiments, the ML model answer engine may be arranged analyze ML model envelopes or ML models to identify portions of segments of the ML models that should be co-located rather the parallelized. For example, ML models may include sub ML models that may be grouped into segments that may benefit from parallelization. In some embodiments, the design of a ML model may include hints or directives that indicate ML model dependencies or the lack thereof. In other embodiments, the ML model repository may be arranged to monitor one or more metrics that may be used by the ML answer engine to determine how to allocate ML models for execution.

In one or more of the various embodiments, the ML model repository may be arranged to monitor one or more metrics, such as, model object copies, data transfers, local queries, or the like, that indicate unidentified ML model dependencies. For example, if one or more metrics indicate that model objects filtered or selected by one ML model are regularly provided to another ML model, the ML answer engine may be arranged automatically modify an affinity score for the two ML models to indicate that they should be considered for co-locating to avoid copying model objects across the network.

Likewise, in one or more of the various embodiments, other metrics may be employed to predict compute or memory resources required for one or more ML models. Accordingly, in one or more of the various embodiments, ML models may be assigned for execution by hosts that may have capabilities that align closer with the performance characteristics of a given ML model. In some embodiments, assignment may be tempered by per customer policies. For example, in some embodiments, if a ML model answer engine determines that a ML model would benefit from higher performing hosts, a customer's individual contract or policy may require execution of the ML model on a lower performance tier. However, in some embodiments, the ML model repository may be arranged to provide reports or notifications to customers indicating that their ML model performance may benefit from a higher tier of service based on observed metrics.

At block 1212, in one or more of the various embodiments, the ML model repository may be arranged to provide one or more reports based on the ML model answers. In one or more of the various embodiments, after the questions provided to the ML model answer engine have been answered, the ML model repository may provide a report that includes the model output associated with the ML models used to answer the question. In some embodiments, the report may be provided in various forms or formats, including, text files, spreadsheets, XML files, or the like. In some embodiments, the report may be formatted to conform to the requirements of one or more reporting or visualization services, or the like. Next, control may be returned to a calling process.

Figure 13:
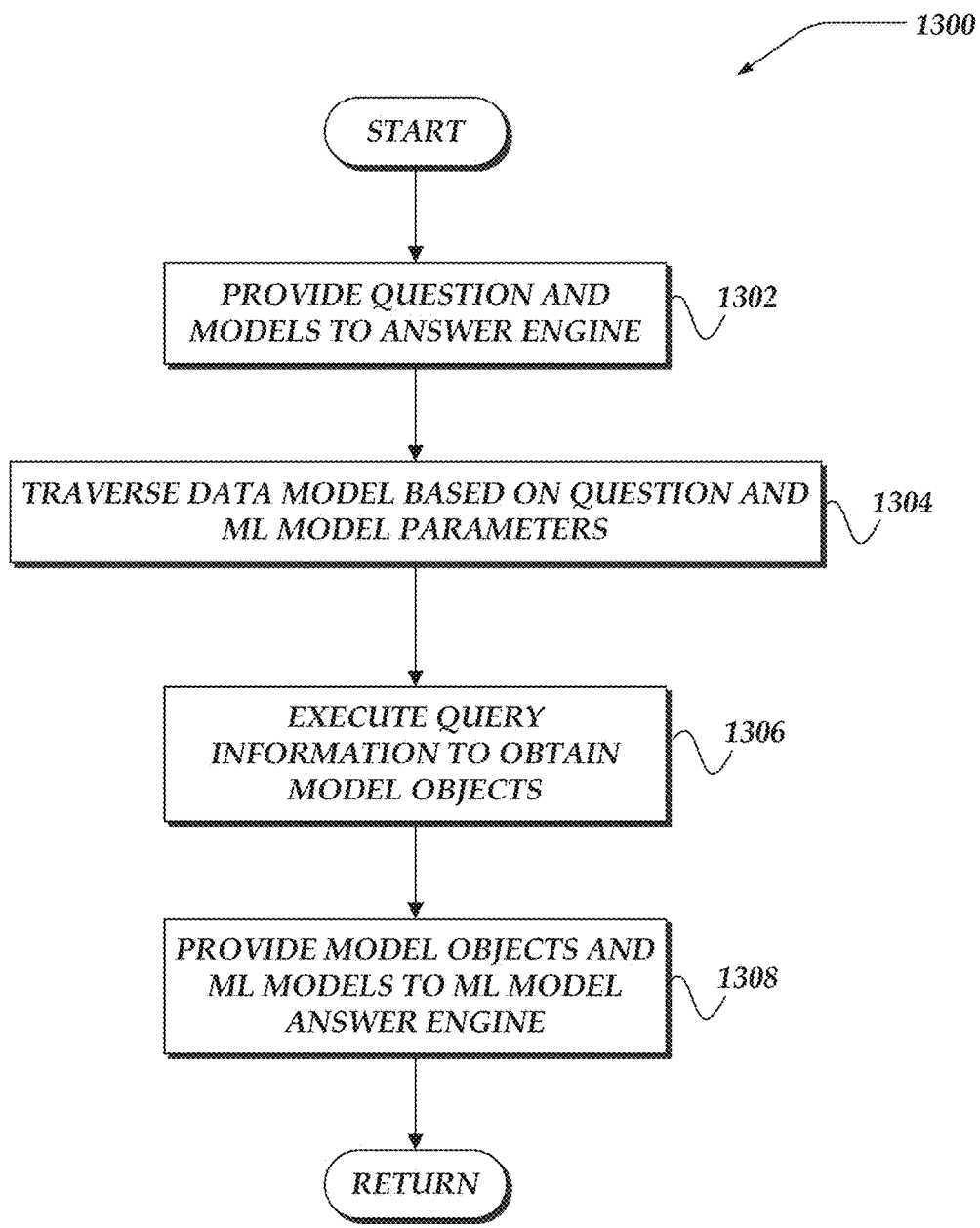
FIG. 13 illustrates a flowchart for a process for employing a machine learning (ML) repository to answer questions in accordance with one or more of the various embodiments.

FIG. 13 illustrates a flowchart for process 1300 for employing a machine learning (ML) repository to answer questions in accordance with one or more of the various embodiments. After a start block, at block 1302, in one or more of the various embodiments, the ML model repository may be arranged to provide a question and one or more ML model envelopes that include one or more ML models to a ML model answer engine.

At block 1304, in one or more of the various embodiments, the ML model answer engine may be arranged to traverse a data model based on the question and the ML model parameter model of the one or more ML models. In some embodiments, if a question requires scoring patient model objects using a particular ML model, the ML model answer engine may be arranged to traverse the data model or model schema to build query information necessary for complying with the input parameter model. For example, if the parameter model is satisfied by model objects representing patients that live in Seattle and have had an encounter (appointment), the model schema may be traversed to provide query information to meet this requirement. In some cases, the model schema or data model may have intervening objects (vertices or nodes) that may need to be traversed to identify the correct query information.

At block 1306, in one or more of the various embodiments, the ML model repository may be arranged to execute a query using the query information to discover model objects eligible for scoring. As discussed above, the ML model repository may be arranged to execute various queries to identify model objects for scoring.

At block 1308, in one or more of the various embodiments, the model objects and ML models may be provided to the ML model answer engine. As discussed above the ML model answer engine may allocate or provide model objects and ML models to various hosts for execution to determine scores in response to the question. Next, control may be returned to a calling process.

Figure 14:
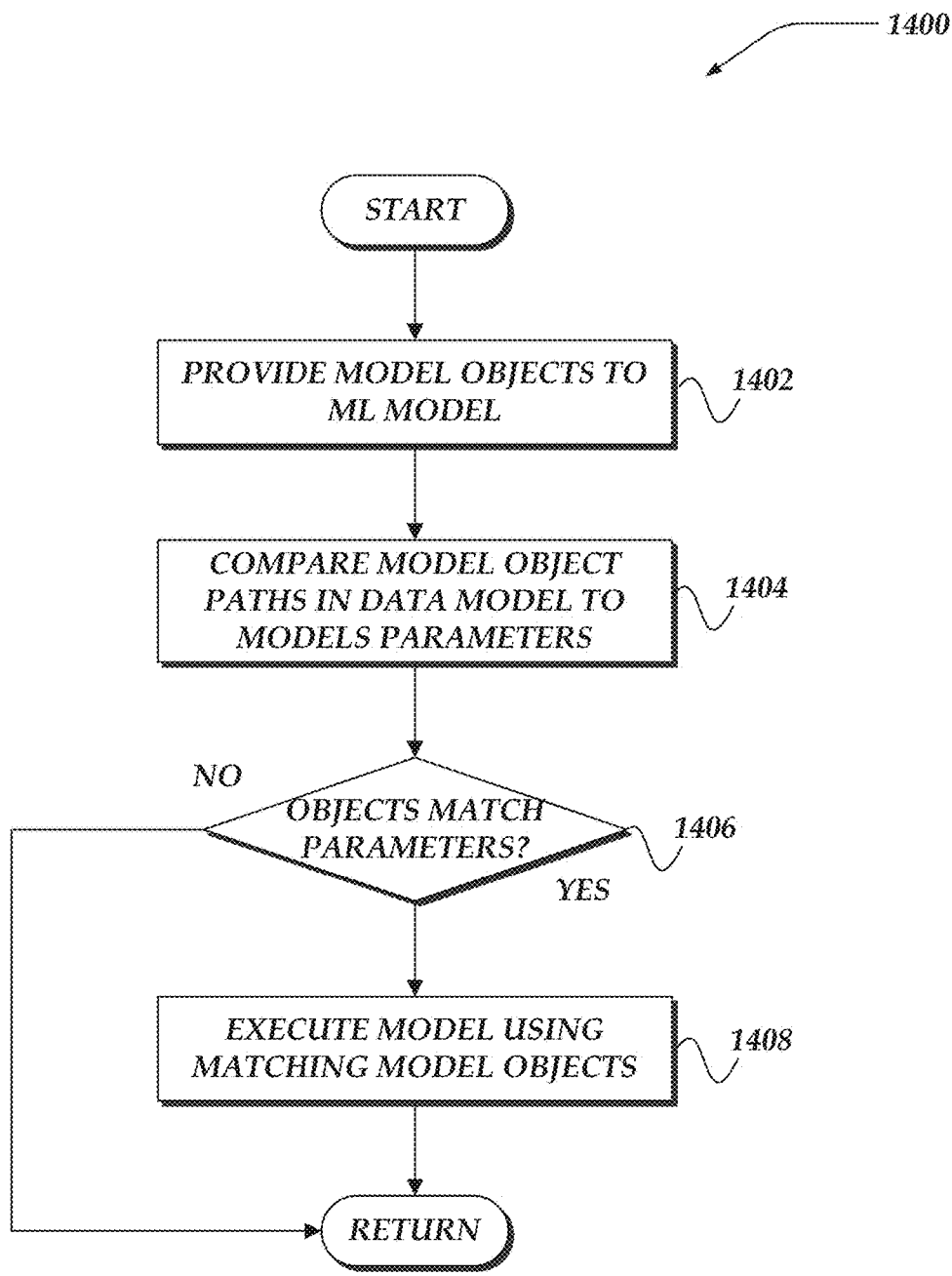
FIG. 14 illustrates a flowchart for a process for employing a machine learning (ML) repository to answer questions in accordance with one or more of the various embodiments.

FIG. 14 illustrates a flowchart for process 1400 for employing a machine learning (ML) repository to answer questions in accordance with one or more of the various embodiments. After a start block, at block 1402, in one or more of the various embodiments, the ML model repository may be arranged to provide one or more model objects to a ML model envelope or ML model. In one or more of the various embodiments, a ML model answer engine may be arranged to accept one or more model objects and one or more ML models. In some embodiments, because one or more of the model objects may be incompatible with the ML model, the model objects may be represented using a model object path corresponding to the model schema or data model rather than the model objects themselves.

At block 1404, in one or more of the various embodiments, the ML model repository may be arranged to compare the model object traversal paths in the data model or model schema with the parameter model. In one or more of the various embodiments, the comparison may include comparing paths in the model schema that may correspond to the ML model's parameters. In one or more of the various embodiments, the comparison may check if the provided model objects include the model object fields or relationships to other model objects included in the parameter model.

At decision block 1406, in one or more of the various embodiments, if the model objects satisfy the ML model's parameter model requirements, control may flow to block 1408; otherwise, control may be returned to a calling process.

At block 1408, in one or more of the various embodiments, the ML model answer engine may be arranged to execute the ML model using the model objects that satisfy its parameter model. As discussed above, the ML model answer engine may be arranged to allocate ML model envelopes, ML models, model objects, or the like, to one or more hosts for execution. Next, control may be returned to a calling process.

It will be understood that each block of the flowchart illustrations, and combinations of blocks in the flowchart illustrations, can be implemented by computer program instructions. These program instructions may be provided to a processor to produce a machine, such that the instructions, which execute on the processor, create means for implementing the actions specified in the flowchart block or blocks. The computer program instructions may be executed by a processor to cause a series of operational steps to be performed by the processor to produce a computer-implemented process such that the instructions execute on the processor to provide steps for implementing the actions specified in the flowchart block or blocks. The computer program instructions may also cause one or more of the operational steps shown in the blocks of the flowcharts to be performed in parallel. Moreover, some of the steps may also be performed across more than one processor, such as might arise in a multi-processor computer system. In addition, one or more blocks in the flowchart illustration may also be performed concurrently with another one or more blocks, or even in a different sequence than illustrated without departing from the scope or spirit of the invention.

Additionally, one or more steps or blocks may be implemented using embedded logic hardware, such as an Application Specific Integrated Circuit (ASIC), Field Programmable Gate Array (FPGA), Programmable Array Logic (PAL), or the like, instead of a computer program. The embedded logic hardware may directly execute embedded logic to perform some or all of the actions in one or more steps or blocks. Also, in one or more embodiments (not shown in the figures), some or all of the actions of one or more of the steps or blocks may be performed by a hardware microcontroller instead of a CPU. In one or more embodiments, the microcontroller may directly execute its own embedded logic to perform actions and access its own internal memory and its own external Input and Output Interfaces (e.g., hardware pins or wireless transceivers) to perform actions, such as System On a Chip (SOC) or the like.

What is claimed as new and desired to be protected by Letters Patent of the United States is:

1. A method for managing data over a network using one or more processors, included in one or more network computers, to perform actions, comprising:
    instantiating an answer engine to perform further actions, including:
        receiving one or more questions and one or more model objects, wherein the one or more model objects are part of a data model that conforms to a model schema;
        receiving a plurality of machine learning (ML) model envelopes based on the one or more questions;
        comparing the data model to parameter models that are associated with each of the plurality of ML model envelopes, wherein the comparison includes a traversal of the data model and one or more of the parameter models;
        selecting one or more of the plurality of ML model envelopes based on the comparison, wherein one or more traversal paths corresponding to the one or more model objects satisfy the parameter models of each of the selected one or more ML model envelopes;
        executing one or more ML models included in each selected ML model envelope to provide score values for the one or more model objects, wherein the score values are included in a report; and
        providing selective optimization of one or more of performance or storage size for one or more ML model repositories based on one or more characteristics including one or more of model object usage frequency, number of model objects in a query result, model object size, or model object data type, wherein the one or more selective optimizations include one or more of indices to improve identification of each model object to be omitted from the one or more traversal paths, or storing a portion of the one or more model objects in a database or a fast data store.

2. The method of claim 1, further comprising:
    instantiating a model training engine to perform actions, including:
        receiving a training data set comprised of a plurality of model objects, wherein the plurality of model objects include one or more of model objects provided in a customer data set, or model objects provided in a validation data set; and
        training the one or more of the ML models included in the plurality of ML model envelopes using the training data set.

3. The method of claim 1, wherein comparing the data model to the parameter models, further includes, employing one or more indices to identify model objects that match the parameter models of the selected one or more ML model envelopes, wherein each model object identified using the one or more indices are omitted from the one or more traversal paths of the data model.

4. The method of claim 1, wherein executing the one or more ML models, further comprises, distributing the execution of the one or more ML models to one or more network computers, wherein two or more ML models that are associated with each other are distributed to the same network computer.

5. The method of claim 1, further comprising:
instantiating an ingestion engine to perform actions, including:
receiving one or more raw data objects; and
executing one or more ingestion rules to transform the one or more raw data objects into the one or more model objects based on the model schema.

6. The method of claim 1, wherein the answer engine performs further actions, comprising:
providing query information based on the question and the model schema;
executing the query information to provide the one or more model objects; and
employing geo-location information provided by a global positioning system (GPS) device at a client computer to determine one or more features that are included in a visual presentation to improve a user's understanding of the report, wherein these features include one or more of time zones, languages, currencies, or calendar formatting that is visually displayed in the report to the user of the client computer when the client computer is located at a particular geo-location.

7. The method of claim 1, further comprising:
instantiating an ingestion engine to perform actions, including:
adding one or more model objects to a customer data set; and
modifying one or more other data models that include the added model objects based on their relationships with other previously provided model objects.

8. The method of claim 1, wherein receiving the one or more model objects, further comprises:
providing the one or more raw data model objects in real-time;
employing an ingestion engine to transform the one or more raw data objects into one or more model objects; and
employing the answer engine to score the one or more model objects.

9. A system for managing data, comprising:
a network computer, comprising:
a transceiver that communicates over the network;
a memory that stores at least instructions; and
one or more processor devices that execute instructions that perform actions, including:
instantiating an answer engine to perform further actions, including:
receiving one or more questions and one or more model objects, wherein the one or more model objects are part of a data model that conforms to a model schema;
receiving a plurality of machine learning (ML) model envelopes based on the one or more questions;
comparing the data model to parameter models that are associated with each of the plurality of ML model envelopes, wherein the comparison includes a traversal of the data model and one or more of the parameter models;
selecting one or more of the plurality of ML model envelopes based on the comparison, wherein one or more traversal paths corresponding to the one or more model objects satisfy the parameter models of each of the selected one or more ML model envelopes;
executing one or more ML models included in each selected ML model envelope to provide score values for the one or more model objects, wherein the score values are included in a report; and
providing selective optimization of one or more of performance or storage size for one or more ML model repositories based on one or more characteristics including one or more of model object usage frequency, number of model objects in a query result, model object size, or model object data type, wherein the one or more selective optimizations include one or more of indices to improve identification of each model object to be omitted from the one or more traversal paths, or storing a portion of the one or more model objects in a database or a fast data store; and
the client computer, comprising:
a client computer transceiver that communicates over the network;
a client computer memory that stores at least instructions; and
one or more processor devices that execute instructions that perform actions, including:
providing the one or more questions; and
displaying the visual representation of the report on a hardware display to the user.

10. The system of claim 9, further comprising:
instantiating a model training engine to perform actions, including:
receiving a training data set comprised of a plurality of model objects, wherein the plurality of model objects include one or more of model objects provided in a customer data set, or model objects provided in a validation data set; and
training the one or more of the ML models included in the plurality of ML model envelopes using the training data set.

11. The system of claim 9, wherein comparing the data model to the parameter models, further includes, employing one or more indices to identify model objects that match the parameter models of the selected one or more ML model envelopes, wherein each model object identified using the one or more indices are omitted from the one or more traversal paths of the data model.

12. The system of claim 9, wherein executing the one or more ML models, further comprises, distributing the execution of the one or more ML models to one or more network computers, wherein two or more ML models that are associated with each other are distributed to the same network computer.

13. The system of claim 9, further comprising:
instantiating an ingestion engine to perform actions, including:
receiving one or more raw data objects; and
executing one or more ingestion rules to transform the one or more raw data objects into the one or more model objects based on the model schema.

14. The system of claim 9, wherein the answer engine performs further actions, comprising:
providing query information based on the question and the model schema;
executing the query information to provide the one or more model objects; and employing geo-location information provided by a global positioning system (GPS) device at a client computer to determine one or more features that are included in a visual presentation to improve a user's understanding of the report, wherein these features include one or more of time zones, languages, currencies, or calendar formatting that is visually displayed in the report to the user of the client computer when the client computer is located at a particular geo-location.

15. The system of claim 9, further comprising:
instantiating an ingestion engine to perform actions, including:
adding one or more model objects to a customer data set; and
modifying one or more other data models that include the added model objects based on their relationships with other previously provided model objects.

16. The system of claim 9, wherein receiving the one or more model objects, further comprises:
providing the one or more raw data model objects in real-time;
employing an ingestion engine to transform the one or more raw data objects into one or more model objects; and
employing the answer engine to score the one or more model objects.

17. A processor readable non-transitory storage media that includes instructions for managing data, wherein execution of the instructions by one or more hardware processors performs actions, comprising:
instantiating an answer engine to perform further actions, including:
receiving one or more questions and one or more model objects, wherein the one or more model objects are part of a data model that conforms to a model schema;
receiving a plurality of machine learning (ML) model envelopes based on the one or more questions;
comparing the data model to parameter models that are associated with each of the plurality of ML model envelopes, wherein the comparison includes a traversal of the data model and one or more of the parameter models;
selecting one or more of the plurality of ML model envelopes based on the comparison, wherein one or more traversal paths corresponding to the one or more model objects satisfy the parameter models of each of the selected one or more ML model envelopes;
executing one or more ML models included in each selected ML model envelope to provide score values for the one or more model objects, wherein the score values are included in a report; and
providing selective optimization of one or more of performance or storage size for one or more ML model repositories based on one or more characteristics including one or more of model object usage frequency, number of model objects in a query result, model object size, or model object data type, wherein the one or more selective optimizations include one or more of indices to improve identification of each model object to be omitted from the one or more traversal paths, or storing a portion of the one or more model objects in a database or a fast data store.

18. The media of claim 17, further comprising:
instantiating a model training engine to perform actions, including:
receiving a training data set comprised of a plurality of model objects, wherein the plurality of model objects include one or more of model objects provided in a customer data set, or model objects provided in a validation data set; and
training the one or more of the ML models included in the plurality of ML model envelopes using the training data set.

19. The media of claim 17, wherein comparing the data model to the parameter models, further includes, employing one or more indices to identify model objects that match the parameter models of the selected one or more ML model envelopes, wherein each model object identified using the one or more indices are omitted from the one or more traversal paths of the data model.

20. The media of claim 17, wherein executing the one or more ML models, further comprises, distributing the execution of the one or more ML models to one or more network computers, wherein two or more ML models that are associated with each other are distributed to the same network computer.

21. The media of claim 17, further comprising:
instantiating an ingestion engine to perform actions, including:
receiving one or more raw data objects; and
executing one or more ingestion rules to transform the one or more raw data objects into the one or more model objects based on the model schema.

22. The media of claim 17, wherein the answer engine performs further actions, comprising:
providing query information based on the question and the model schema;
executing the query information to provide the one or more model objects; and
employing geo-location information provided by a global positioning system (GPS) device at a client computer to determine one or more features that are included in a visual presentation to improve a user's understanding of the report, wherein these features include one or more of time zones, languages, currencies, or calendar formatting that is visually displayed in the report to the user of the client computer when the client computer is located at a particular geo-location.

23. The media of claim 17, further comprising:
instantiating an ingestion engine to perform actions, including:
adding one or more model objects to a customer data set; and
modifying one or more other data models that include the added model objects based on their relationships with other previously provided model objects.

24. A network computer for managing data, comprising:
a transceiver that communicates over the network;
a memory that stores at least instructions; and
one or more processor devices that execute instructions that perform actions, including:
instantiating an answer engine to perform further actions, including:
receiving one or more questions and one or more model objects, wherein the one or more model objects are part of a data model that conforms to a model schema;
receiving a plurality of machine learning (ML) model envelopes based on the one or more questions;
comparing the data model to parameter models that are associated with each of the plurality of ML model envelopes, wherein the comparison includes a traversal of the data model and one or more of the parameter models;

selecting one or more of the plurality of ML model envelopes based on the comparison, wherein one or more traversal paths corresponding to the one or more model objects satisfy the parameter models of each of the selected one or more ML model envelopes;

executing one or more ML models included in each selected ML model envelope to provide score values for the one or more model objects, wherein the score values are included in a report; and providing selective optimization of one or more of performance or storage size for one or more ML model repositories based on one or more characteristics including one or more of model object usage frequency, number of model objects in a query result, model object size, or model object data type, wherein the one or more selective optimizations include one or more of indices to improve identification of each model object to be omitted from the one or more traversal paths, or storing a portion of the one or more model objects in a database or a fast data store.

25. The network computer of claim 24, further comprising:

instantiating a model training engine to perform actions, including:

receiving a training data set comprised of a plurality of model objects, wherein the plurality of model objects include one or more of model objects provided in a customer data set, or model objects provided in a validation data set; and training the one or more of the ML models included in the plurality of ML model envelopes using the training data set.

26. The network computer of claim 24, wherein comparing the data model to the parameter models, further includes, employing one or more indices to identify model objects that match the parameter models of the selected one or more ML model envelopes, wherein each model object identified using the one or more indices are omitted from the one or more traversal paths of the data model.

27. The network computer of claim 24, wherein executing the one or more ML models, further comprises, distributing the execution of the one or more ML models to one or more network computers, wherein two or more ML models that are associated with each other are distributed to the same network computer.

28. The network computer of claim 24, further comprising:

instantiating an ingestion engine to perform actions, including:

receiving one or more raw data objects; and executing one or more ingestion rules to transform the one or more raw data objects into the one or more model objects based on the model schema.

29. The network computer of claim 24, further comprising:

instantiating an ingestion engine to perform actions, including:

adding one or more model objects to a customer data set; and modifying one or more other data models that include the added model objects based on their relationships with other previously provided model objects.

30. The network computer of claim 24, wherein receiving the one or more model objects, further comprises:

providing the one or more raw data model objects in real-time;

employing an ingestion engine to transform the one or more raw data objects into one or more model objects; and employing the answer engine to score the one or more model objects.

* * * * *